United States Patent
Rattner et al.

(10) Patent No.: US 11,751,801 B2
(45) Date of Patent: Sep. 12, 2023

(54) SYSTEMS AND METHOD FOR SKIN ANALYSIS USING ELECTRONIC DEVICES

(71) Applicant: FITSKIN INC., Toronto (CA)

(72) Inventors: Sergio Rattner, Toronto (CA); Dan-razvan Ilies, Salaj (RO)

(73) Assignee: FITSKIN INC., Toronto (CA)

( * ) Notice: Subject to any disclaimer, the term of this patent is extended or adjusted under 35 U.S.C. 154(b) by 600 days.

(21) Appl. No.: 16/095,342

(22) PCT Filed: Apr. 21, 2017

(86) PCT No.: PCT/CA2017/050503
§ 371 (c)(1),
(2) Date: Oct. 19, 2018

(87) PCT Pub. No.: WO2017/181293
PCT Pub. Date: Oct. 26, 2017

(65) Prior Publication Data
US 2019/0125249 A1    May 2, 2019

Related U.S. Application Data

(60) Provisional application No. 62/438,835, filed on Dec. 23, 2016, provisional application No. 62/344,287, (Continued)

(51) Int. Cl.
*A61B 5/00* (2006.01)

(52) U.S. Cl.
CPC ............ *A61B 5/445* (2013.01); *A61B 5/0022* (2013.01); *A61B 5/0077* (2013.01); *A61B 5/442* (2013.01);
(Continued)

(58) Field of Classification Search
CPC ....... A61B 5/445; A61B 5/744; A61B 5/6898; A61B 5/743; A61B 5/0022; A61B 5/0077;
(Continued)

(56) References Cited

U.S. PATENT DOCUMENTS 4,998,821 A * 3/1991 Ohta .................... G03F 7/70891
353/101
6,993,167 B1 * 1/2006 Skladnev ............. A61B 5/0059
382/128

(Continued)

FOREIGN PATENT DOCUMENTS

JP    2010160286 A    7/2010
JP    2014131121 A    7/2014
(Continued)

OTHER PUBLICATIONS

Matias et al., "skin colour, skin redness and melanin biometric measurements: comparison study between Antera 3D, Mexameter and Colorimeter", Skin Research and Technology, vol. 21, No. 3, pp. 346-362, XP055431206 [X] 1-4, 8-9, 17-19.

*Primary Examiner* — Rene T Towa
(74) *Attorney, Agent, or Firm* — Jenna L. R. Wilson; Wilson Lue LLP

(57) ABSTRACT

There is a skin analysis device for attachment to an electronic device of a human user, the electronic device having at least one skin characteristic measurement device, the skin analysis device comprising an enclosure comprising an enclosure body, configured to be removably connected to the electronic device and one or more skin characteristic measurement assisters, connected to the enclosure and configured to assist one or more skin characteristic measurement devices take a skin characteristic sample of a skin characteristic of the human user.

18 Claims, 33 Drawing Sheets

Related U.S. Application Data filed on Jun. 1, 2016, provisional application No. 62/326,558, filed on Apr. 22, 2016.

(52) U.S. Cl.
CPC ............... *A61B 5/443* (2013.01); *A61B 5/444* (2013.01); *A61B 5/6898* (2013.01); *A61B 5/743* (2013.01); *A61B 5/744* (2013.01)

(58) Field of Classification Search
CPC ......... A61B 5/442; A61B 5/443; A61B 5/444; G16H 40/67
See application file for complete search history.

(56) References Cited

U.S. PATENT DOCUMENTS

| | | | |
|---|---|---|---|
| 8,118,740 | B2 | 2/2012 | Howell |
| D753,308 | S | 4/2016 | Marinkovich |
| 9,325,884 | B2 | 4/2016 | Fletcher et al. |
| 9,547,218 | B2 | 1/2017 | Takahashi et al. |
| 2004/0125996 | A1* | 7/2004 | Eddowes ............... A61B 5/442 382/128 |
| 2006/0239547 | A1 | 10/2006 | Robinson |
| 2012/0172685 | A1 | 7/2012 | Gilbert |
| 2012/0231841 | A1* | 9/2012 | Niederberger .......... H04M 1/21 455/556.1 |
| 2013/0130753 | A1 | 5/2013 | Springer |
| 2013/0300919 | A1 | 11/2013 | Fletcher et al. |
| 2013/0322711 | A1 | 12/2013 | Schultz et al. |
| 2014/0243685 | A1* | 8/2014 | Patwardhan ......... A61B 5/0077 600/476 |
| 2015/0025343 | A1* | 1/2015 | Gareau ................ A61B 5/0075 600/328 |
| 2015/0042877 | A1 | 2/2015 | O'Neil et al. |
| 2015/0085279 | A1 | 3/2015 | Balooch et al. |
| 2015/0355527 | A1* | 12/2015 | Takahashi ........ H04N 5/232935 348/371 |

FOREIGN PATENT DOCUMENTS

| | | |
|---|---|---|
| KR | 10-2010-0005072 | 1/2010 |
| KR | 10-2013-0057148 | 5/2013 |
| WO | 2015/013288 A2 | 1/2015 |

* cited by examiner

Fig. 9 Assembly

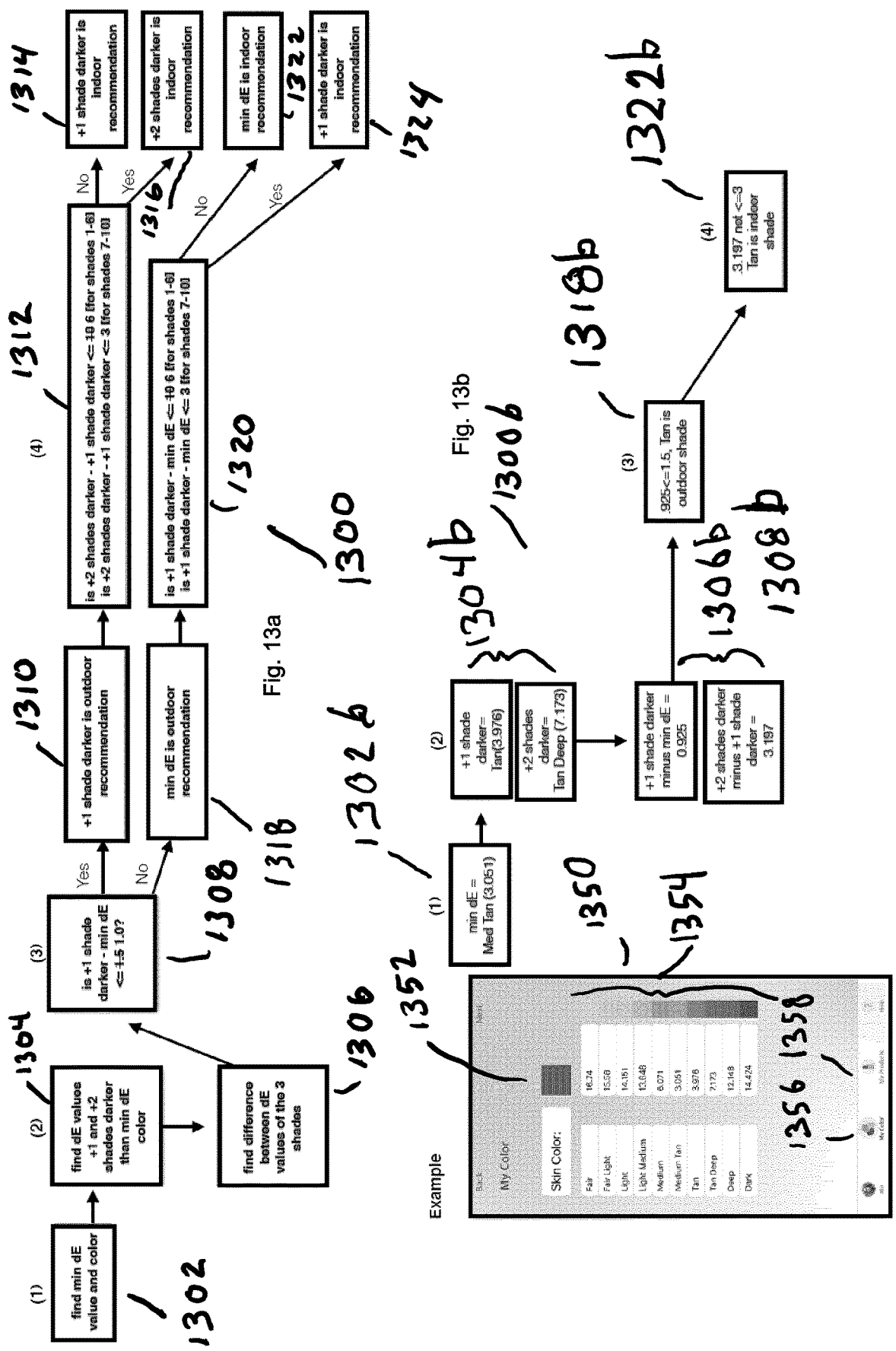

Fig. 16a
Fig. 16b
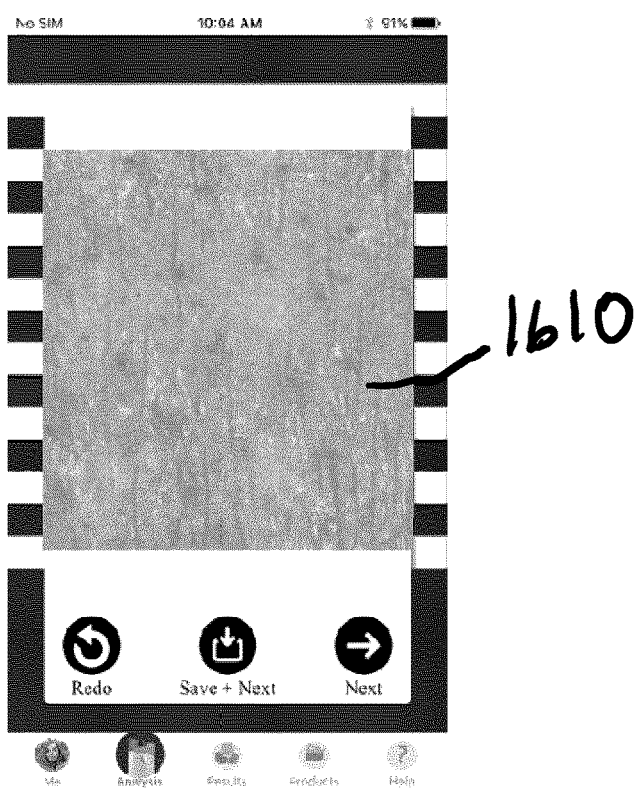
Analyzed Image (Pores)

Fig. 16c
Fig. 16d
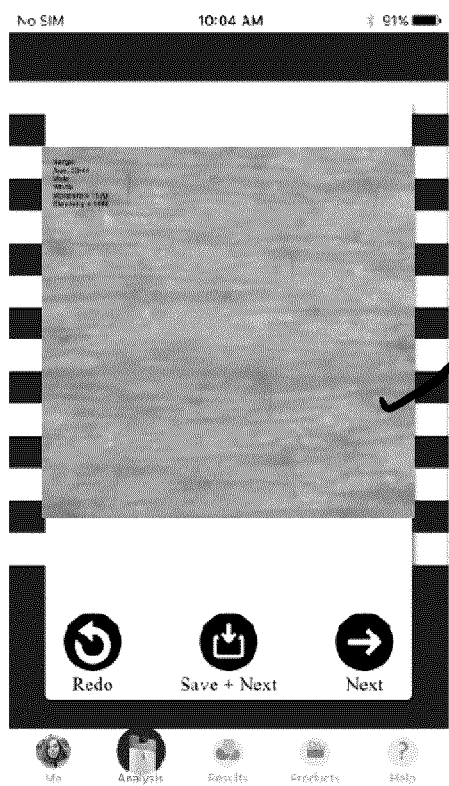
Analyzed Image (Lines)

Fig. 16e
Fig. 16f
Analyzed Image (Oil)

SYSTEMS AND METHOD FOR SKIN ANALYSIS USING ELECTRONIC DEVICES

CROSS-REFERENCE TO RELATED APPLICATIONS

This application claims priority from U.S. Provisional Application No. 62/438,835, filed on Dec. 23, 2016, from U.S. Provisional Application No. 62/344,287 filed on Jun. 1, 2016, and from U.S. Provisional Application No. 62/326,558 filed on Apr. 22, 2016, the contents of all of which, in their entirety, are herein incorporated by reference.

TECHNICAL FIELD

The present invention relates to measurement and analysis of skin characteristics and in particular to systems and methods of measuring skin characteristics using skin analysis devices that attach to smartphones, and sharing the measurements so as to provide recommended skin care and cosmetics products based on the skin analysis.

BACKGROUND

Skin care product manufacturers create skin care products to assist users with maintaining healthy and beautiful skin. However, one of the biggest problems in the consumer skin care and cosmetics industries are the difficulties in assessing skin type, the inability to quantitatively and objectively demonstrate that a skin care product is effective, and the difficulty in matching cosmetics colors to a consumers' specific skin tones.

Various solutions exist that attempt to address at least some of these challenges. However, limitations and failures of these solutions abound. For example existing solutions suffer from one or more of the following limitations:
  (a) Inaccuracy in measurements. For example caused by technical limitations, unrealistic requirements of a user, and the like.
  (b) Too limited a scope of measurement capability. For example only measuring one or two skin care characteristic when two or more are required to effectively recommend skin care products or provide skin analysis.
  (c) Cost. For example most solutions are stand-alone device that do not leverage existing technology and high end components. Therefore the solutions include all components that are required for the various measurements, and all the product design needed. This makes such solutions prohibitively expensive.
  (d) Logistic challenges in deploying solutions. Specialized hardware is difficult to deploy, particularly when it is expensive. Hardware that is difficult to calibrate, maintain, or use is similarly difficult to deploy in a way that it will be used, and used accurately.

There is accordingly a need in the art for an improved method and system capable of skin analysis using electronic devices such as smartphones.

SUMMARY OF THE INVENTION

In a first embodiment of the invention, there is disclosed a skin analysis device for attachment to an electronic device of a user, the electronic device having at least one skin characteristic measurement device, the skin analysis device comprising:
  an enclosure comprising an enclosure body, configured to be removably connected to the electronic device;
  one or more passive skin characteristic measurement assisters, connected to the enclosure and configured to assist one or more skin characteristic measurement devices take a skin characteristic sample of a skin characteristic of the user.

In one aspect of the first embodiment the at least one skin characteristic measurement device is a camera and the one or more passive skin characteristic measurement assisters comprise a lens, disposed in front of the camera when the enclosure is connected to the electronic device.

In another aspect of the first embodiment the at least one skin characteristic measurement device is a camera and the one or more passive skin characteristic measurement assisters comprise a color calibrator assembly, disposed in front of the camera when the enclosure is connected to the electronic device.

In another aspect of the first embodiment the color calibrator assembly comprises: a sleeve, through which the camera takes a picture, a color calibrator disposed on an inside surface of the sleeve, and a skin contact ring.

In another aspect of the first embodiment the at least one skin characteristic measurement device is a camera and the one or more passive skin characteristic measurement assisters comprise a light source assembly, wherein the light source assembly comprises:
  a light source board with one or more individually controllable light sources thereon that illuminate the user when the camera captures an image of the user;
  a diffuser that diffuses one or more light sources that pass through the diffuser, the light source board comprising one or more light source apertures located therein that allow light sources to pass therethrough undiffused;
  a set of first light sources providing a first light source, disposed on the light source board such that the first light source does not pass through the light source apertures and is diffused by the diffuser.

In another aspect of the first embodiment the light source assembly further comprises a set of second light sources providing a second light source, disposed on the light source board such that the second light source passes through the light source apertures undiffused.

In another aspect of the first embodiment the set of first light sources are light emitting diode lights providing light emitting diode light and the set of second light sources are ultraviolet lights providing ultraviolet light.

In another aspect of the first embodiment the skin analysis device further comprises:
  one or more active skin characteristic measurement assisters, connected to the enclosure and configured to assist the one or more skin characteristic measurement devices take a skin characteristic sample of a skin characteristic of the user; and
  a skin analysis device processor, in communication with the electronic device and the one or more active skin characteristic measurement assisters, the skin analysis device processor configured to:
    receive a sample taking signal from the electronic device; and
    control the one or more active skin characteristic measurement assisters to assist the one or more skin characteristic measurement devices take a skin characteristic sample.

In another aspect of the first embodiment the one or more active skin characteristic measurement assisters comprise a light source assembly.

In another aspect of the first embodiment the light source assembly further comprises a first light source and a second light source, wherein the first light source is a light emitting diode (LED) light source and the second light source is an ultraviolet (UV) light source.

In another aspect of the first embodiment the skin analysis device further comprises a diffuser, configured to be between the light source board and the user, and configured to diffuse the first light source and not diffuse the second light source.

In another aspect of the first embodiment the skin analysis device processor further comprises a Bluetooth transceiver and the sample taking signal is received from a Bluetooth transceiver of the electronic device.

In another aspect of the first embodiment the skin analysis device further comprises:
  a second skin characteristic measurement device, connected to the enclosure and configured to take a second skin characteristic sample of a skin characteristic of the user; and
  a skin analysis device processor, in communication with the electronic device and the second skin characteristic measurement device, the skin analysis device processor configured to:
    obtain a second skin characteristic sample from the second skin characteristic measurement device; and
    provide the second skin characteristic sample to the electronic device.

In another aspect of the first embodiment the skin analysis device processor is further configured to:
  receive a sample taking signal from the electronic device; and
  control the second skin characteristic measurement device to take the second skin characteristic sample.

In another aspect of the first embodiment the second skin characteristic measurement devices comprise a moisture sensor.

In another aspect of the first embodiment the skin analysis device processor further comprises a Bluetooth transceiver and the sample taking signal is received from a Bluetooth transceiver of the electronic device.

In another aspect of the first embodiment the enclosure further comprises a cylindrical sleeve assembly aperture configured to be disposed in front of a camera of the electronic device when the skin analysis device is attached to the electronic device In another aspect of the first embodiment the cylindrical sleeve assembly aperture is further configured to receive a skin characteristic measurement assister.

In another aspect of the first embodiment the skin analysis device further comprises an app, installed and operating on the electronic device, configured to:
  communicate with the skin analysis device and the electronic device to facilitate obtaining the skin characteristic sample from the at least one skin characteristic measurement device.

In a second embodiment of the invention there is disclosed a system for performing one or more skin characteristic analyses, the system comprising:
  a skin characteristic application, operating on an electronic device having a camera that can take images of a user, the skin characteristic application configured to:
    control the camera to take a set of images of the user;
    perform a set of skin care processings on the set of images to obtain a set of skin analysis measurements;
    communicate with a skin analysis device to:
      send an activation signal to a moisture sensor to initiate a moisture sensor reading; and
      receive a moisture sensor reading from the moisture sensor;
  a skin analysis device connected to the electronic device, comprising:
    a processor, configured to:
      receive an activation signal from the skin characteristic application;
      in response to the activation signal, obtain a moisture sensor reading from the moisture sensor; and
      send the moisture sensor reading to the skin characteristic application;
    a moisture sensor configured to:
      send a moisture sensor reading to the processor.

In one aspect of the second embodiment the set of skin care processings comprise sunscreen processings, and color matching.

In another aspect of the second embodiment the set of skin care processings comprises lines processings and lines processings further comprises:
  converting the image to a L*ab color;
  eliminating hair;
  applying a high pass filter;
  changing the image to black and white;
  using a morphological skeleton to identify possible lines and wrinkles;
  applying a Hough transform; and
  inverting the image such that a line in the image is white.

In another aspect of the second embodiment the set of skin care processings comprises pores processings and pores processings further comprises:
  converting the image to a grayscale image having a grayscale matrix;
  calculating a mean value of the grayscale matrix:
  subtracting each grayscale matrix element from the mean value to obtain a new grayscale matrix.
  for each pixel, having a pixel color, of the new grayscale matrix:
    consider a window of pixels around the pixel;
    count the pixels, in the window of pixels, having a pixel color value in a specified range;
    if more than a first quantity of pixels in the window of pixels are counted then set the pixel color as white and increase a white pixel counter by one, otherwise set the pixel color as black; and
  set the white pixel counter as a pore score.

In another aspect of the second embodiment the skin characteristic application is further configured to activate an ultraviolet light source when taking the set of images;
  the set of images comprises an image before applying sunscreen and one or more images after applying sunscreen; and
  wherein the set of skin care processings comprises sunscreen processings, and sunscreen processings further comprises:
    calculating a blue score for the set of images;
    comparing the blue score to a threshold blue score; and
    indicating to re-apply sunscreen if the blue score exceeds the threshold blue score.

In another aspect of the second embodiment the set of images further comprises an image before applying sunscreen and comparing further comprises determining a difference between the blue score of the image before applying sunscreen to the image after applying sunscreen and the indicating further comprises indicating if the difference between the blue score of the image before applying sunscreen to the image after applying sunscreen exceeds a reduction threshold.

In a third embodiment of the invention there is disclose a skin analysis device for attachment to an electronic device of a user, the skin analysis device comprising:
  an enclosure comprising an enclosure body, configured to be removably connected to the electronic device, and a cylindrical sleeve assembly aperture configured to receive a cylindrical sleeve assembly and be disposed in front of a camera of the electronic device when the skin analysis device is attached to the electronic device;
  a lens, attachedly inserted in the cylindrical sleeve assembly aperture, radially closer to the camera than a first light source;
  a cylindrical sleeve assembly, attachedly inserted in the cylindrical sleeve assembly aperture, comprising:
    a cylindrical sleeve;
    a moisture sensor disposed on the cylindrical sleeve assembly such that the moisture sensor can measure moisture qualities of a surface of the user when the skin analysis device is in a measuring mode, the moisture sensor in communication with a skin analysis device processor; and
    a light source assembly, that diffuses light from a first light source located thereon, disposed in front of the camera when the skin analysis device is attached to the electronic device, the light source assembly in communication with the skin analysis device processor;
  the skin analysis device processor, in communication with the electronic device, the moisture sensor and the light source assembly, the skin analysis device processor configured to facilitate one or more skin analysis analyses; and
  a battery, to provide power to the skin analysis device processor.

In a fourth embodiment of the invention there is a system for collection, dissemination and use of skin characteristic samples, from a set of users and obtained from a user's electronic device, the system comprising:
  a set of skin characteristic applications, installed on each of a set of electronic devices, each skin characteristic application configured to:
    facilitate collection of a skin characteristic sample for a user from one or more skin characteristic measurement devices;
    create a skin characteristic sample data structure from the skin characteristic sample;
    allow a first skin analysis based on the skin characteristic sample data structure to produce results.

In one aspect of the further embodiment the skin characteristic application is further configured to: show the results of the first skin analysis.

In another aspect of the fourth embodiment the skin characteristic application is further configured to:
  perform a product recommendation algorithm based on the first skin analysis; and
  recommend one or more recommended products based on the product recommendation algorithm.

In another aspect of the fourth embodiment the skin characteristic application is further configured to:
  provide one or more screens for purchasing a recommended product.

In another aspect of the fourth embodiment the skin characteristic application is further configured to
  communicate the skin characteristic sample data structures to a skin analysis server; and
wherein the system further comprises a skin analysis server configured to:
  receive the skin characteristic sample data structures from the set of electronic devices; and
  store the skin characteristic sample data structures in a storage device.

In another aspect of the fourth embodiment the skin analysis server is further configured to:
  calculate one or more relative scores from the skin characteristic sample; and
  disseminate the one or more relative scores to a user's electronic device.

In another aspect of the fourth embodiment the skin characteristic application is further configured to:
  communicate the skin characteristic sample data structures to a product owner server of a product owner; and
wherein the system further comprises the product owner server configured to:
  receive the skin characteristic sample data structures from the set of electronic devices; and
  store the skin characteristic sample data structures in a storage device.

In another aspect of the fourth embodiment the skin characteristic sample data structures further comprises a user referrer and the skin characteristic application is further configured to communicate if the product owner is the user referrer.

In another aspect of the fourth embodiment the user referrer is established upon installing the skin characteristic application on the user's electronic device or based on a skin analysis device identifier of a skin analysis device attached to the user's electronic device.

In another aspect of the fourth embodiment the product owner server is further configured to:
  obtain the first skin analysis;
  perform a product recommendation algorithm based on the first skin analysis;
  recommend one or more recommended products based on the product recommendation algorithm; and
  provide the one or more recommended products to the user's electronic device.

In a fifth embodiment of the invention there is a method for matching a user's face color to a suggested product color for an assumed lighting from a total color options, the method comprising:
  obtaining a set of images of the user's face wherein each image in the set of images comprises a user portion and a color calibration portion, wherein the color calibration portion comprises at least one color quadrant of a color calibrator having a known color;
  for each image in the set of images:
    perform a color correction transform on the user portion based on the color calibration portion;
    remove outlier pixels from the user portion;
    determine an average color for the user portion;
  averaging each of the average colors for the user portions to arrive at a determined color for the user;
  comparing determined color to the total color options to arrive at the suggested product color;
  communicating the suggested product color.

In one aspect of the fifth embodiment the obtaining is from a camera of an electronic device having a camera with a skin analysis device attached thereon, the color calibrator being disposed on the skin analysis device.

In another aspect of the fifth embodiment the comparing further comprises:
  arriving at a color difference, between the determined color and a set of colors in the total color options;

selecting the color having the minimum color difference as the suggested product color.

In another aspect of the fifth embodiment the arriving further comprises applying a hue filter to the colors in the total color options to get the set of colors.

In another aspect of the fifth embodiment the method further comprises:
specifying one or more alternative lightings or one or more moods;
determining if the one or more alternative lightings or one or more moods alter the suggested product color, and if so:
arriving at one more contextual suggested product colors; and
communicating the contextual suggested product colors.

In a sixth embodiment of the invention there is disclosed a system for measuring elasticity of a user's skin, the user's skin having an original position when the user's skin is at rest, the system comprising:
an electronic device, proximate the user's skin such that the user's skin moves in response to a vibration motor, the electronic device comprising:
a camera, capable of recording video and being controllable by a skin characteristic application;
a vibration motor that causes the electronic device to vibrate and being controllable by the skin characteristic application;
the skin characteristic application, configured to:
activate the vibration motor when the camera is positioned to capture a video of the user's skin;
causing the camera to record the video;
deactivate the vibration motor after a period of time; and
process the video to calculate an elasticity score.

In one aspect of the sixth embodiment the skin characteristic application is further configured to process the video by measuring an amount of time for the user's skin to return to the original position.

In another aspect of the sixth embodiment the skin characteristic application is further configured to activate a set of bursts of the vibration motor and to process a set of amounts of time for the user's skin to return to the original position.

In another aspect of the sixth embodiment the system further comprises a skin analysis device for attachment to the electronic device, the skin analysis device comprising a sleeve with a lens disposed on an inside surface of the sleeve, through which the camera takes a picture, and a skin contact ring that is contact with the user's skin when the camera is positioned to capture a video of the user's skin.

In a seventh embodiment of the invention there is a color calibrator assembly for ensuring an image of a user, taken with a camera of an electronic device having a field of view, is of known color, the color calibrator assembly comprising:
a sleeve, attached to the electronic device and disposed on top of the camera, axially through which the camera takes a picture of the field of view;
a color calibrator disposed on an inside surface of the sleeve and obscuring a portion of the field of view; and a skin contact ring configured to be in contact with the user, at a user contact point, when the image is taken.

In one aspect of the seventh embodiment the color calibrator assembly of claim 46 wherein the color calibrator further comprises a color ring having one or more color quadrants, each of the one or more color quadrants having a known color.

In another aspect of the seventh embodiment the color calibrator assembly further comprises a color calibrator assembly attachment that removably attaches the color calibrator assembly to the electronic device at an attachment point.

In another aspect of the seventh embodiment the sleeve, the attachment point and the user contact point all prevent light from entering the color calibrator assembly.

In another aspect of the seventh embodiment the color calibrator assembly further comprises a light source, disposed axially along the sleeve, and configured to add light, of a known color, to the field of view when the image is taken.

In another aspect of the seventh embodiment the color calibrator assembly attachment is configured to cover a flash of the electronic device and prevent a light from the flash of the electronic device from entering the image.

In an eighth embodiment of the invention there is disclosed a system for calibrating a moisture sensor, that can be pressed into contact with a user's skin at an unknown pressure by a user when taking a moisture sensor reading, where pressure affects the moisture sensor reading, the system comprising:
an electronic device comprising:
a camera with a variable focus distance, that has a focus distance when taking an image; and
a skin characteristic application configured to:
facilitate taking a first picture of a test subject at a forceful pressure and recording i) a first focus distance when the first picture was taken and ii) a first moisture sensor reading from the moisture sensor;
implement taking a second picture of the test subject at a light pressure and recording i) a second focus distance when the first picture was taken and ii) a second moisture sensor reading from the moisture sensor;
calculate a pressure-based moisture adjustment slope;
apply the pressure-based moisture adjustment factor to a future moisture sensor reading, taken at a future focus distance, to arrive at an adjusted future moisture sensor reading; and
a moisture sensor, configured to:
provide moisture sensor readings to the skin characteristic application.

In one aspect of the eighth embodiment the skin characteristic application is further configured to:
determine the pressure-based moisture adjustment slope having a first (x/y) point at (the first focal length/the first moisture sensor reading) and a second (x/y) point at (the second focus distance/the second moisture sensor reading); and
quantify an average focus distance from the first focus distance and the second focus distance.

In another aspect of the eighth embodiment the applying further comprises:
solving a slope point form equation of a form $Y-Y1=m(X-X1)$, where
Y is the adjusted future moisture sensor reading;
Y1 is the future moisture sensor reading;
m is the pressure-based moisture adjustment slope;
X is the average focus distance; and
X1 is the future focus distance.

In one aspect of the eighth embodiment the skin characteristic application is further configured to:
prompt a user to select a first focal point near a middle of a display of the electronic device that is previewing the first picture; and
accept a user input selecting the focal point as a trigger to take a picture.

In one aspect of the eighth embodiment the skin characteristic application is further configured to:
ask a user to select a first focal point near a middle of a display of the electronic device that is previewing the first picture; and
receive a user input selecting the focal point as a trigger to take a picture.

In a ninth embodiment of the invention there is disclosed a system for safe use of an adverse effect device, that assists a skin characteristic measurement device take a skin characteristic sample of a user but may be dangerous to the user if used in an improper way, the system comprising:
an electronic device, having a skin characteristic measurement device for taking images and a skin characteristic application configured to:
send an activation signal to the adverse effect device to permit turn on the adverse effect device if a safe use indicator signal is received; and
activate a camera to take an image;
a skin analysis device comprising:
an adverse effect device connected to the skin analysis device and configured to:
assist one or more skin characteristic measurement devices take a skin characteristic sample of a skin characteristic of the user responsive to an activation signal from the skin characteristic application;
a safe use indicator device, configured to:
send a safe use indicator signal to a processor; and
the processor, configured to:
obtain safe use indicator device signal; and
send the safe use indicator device signal to the skin characteristic application.

In one aspect of the ninth embodiment the adverse effect device is a ultraviolet light and the safe use indicator is a moisture sensor.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIGS. 13a-b are methods for color matching for different lighting according to an aspect of the present invention;

FIGS. 16a-f illustrate screenshots of an app for an electronic device, with largely raw images and resultant processed images, according to an aspect of the present invention.

DETAILED DESCRIPTION OF THE INVENTION

Figure 1:
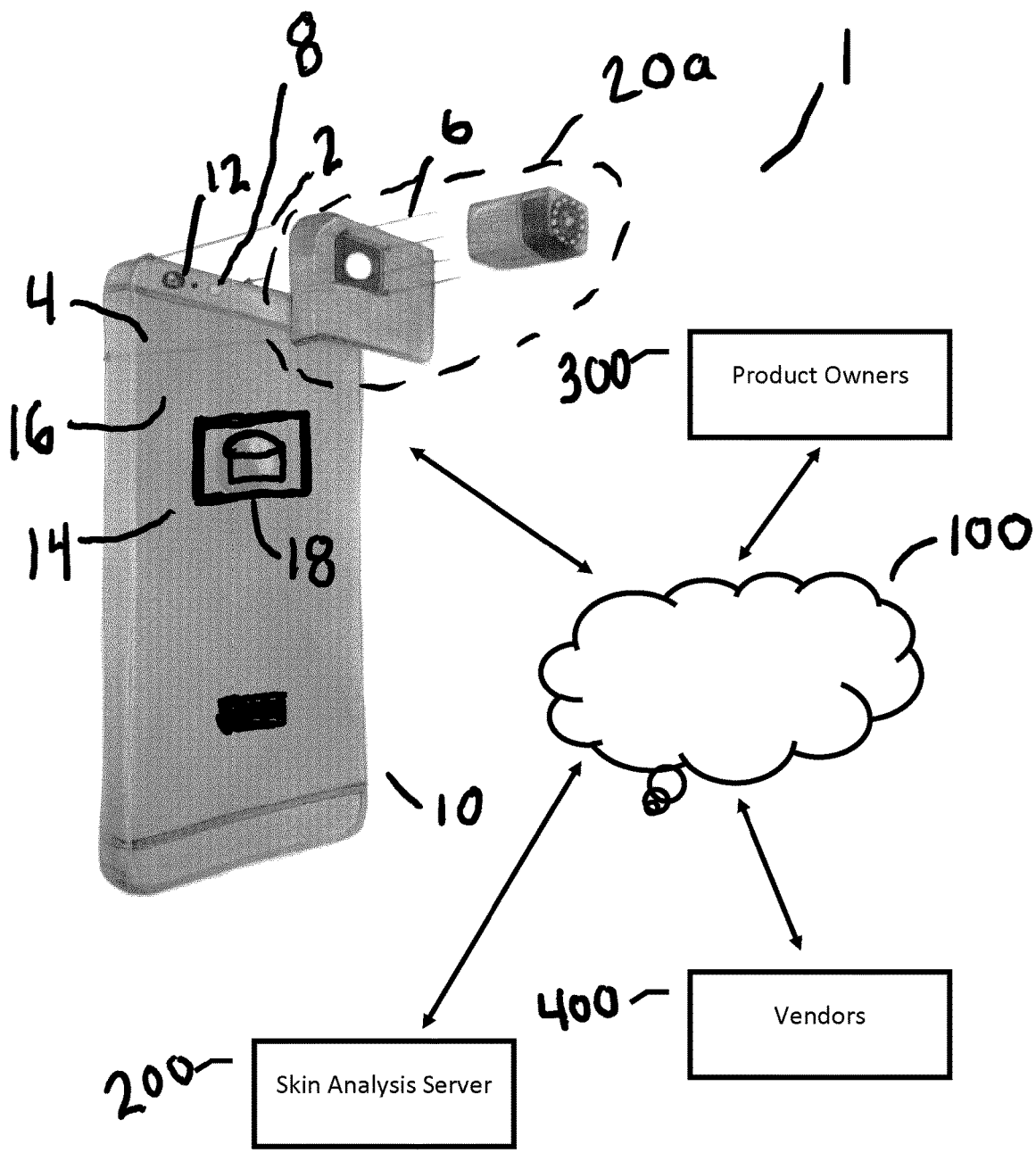
FIG. 1 illustrates aspects of an exemplary electronic device and skin analysis device, and related system, according to an embodiment of the present invention.

Broadly, the invention as herein described is a skin analysis device that attaches to a mobile device and performs one or more skin analysis actions such as capturing images of a human face to assess moisture, pores and the like. Images and other measurements are stored, compared to other samples and used to recommend products to assist with skin care.

As used, and further described herein, the following terms have the following meanings:

(a) Back side: the side of an electronic device that typically faces away from the user when the electronic device is being used by its user and may have a back camera.

(b) Electronic device: a device, having a camera, onto which a skin analysis device can be attached, that may preferably be mobile (such as mobile phones and tablets), exemplary electronic devices including smart phones, tablets, digital cameras, personal computers, televisions and the like.

(c) Front side: the side of an electronic device that typically faces towards the user when the electronic device is being used by its user, and may have a front camera.

(d) Image: Unless specified otherwise, references herein to image(s) refer to digital images that can be represented by digital data capable and can be manipulated and processed by electronic devices and computers (such as app 18, SAS 200, and the like);

(e) Skin characteristics: one or more characteristics of skin (including hair), such as color, moisture, oiliness, elasticity, and the like.

(f) Skin characteristic measurement assisters: components that assist a skin characteristic measurement device in taking a skin care measurement. These may either be generally thought of as passive (ie not requiring control by the electronic device or skin analysis device, such as lens 34, contact ring, sleeve 24 and the like) or active (requiring control etc by the electronic device, such as light source board, and vibration motor).

(g) Skin characteristic measurement device: a component that takes skin analysis actions, either under its own control or the control of another component. These may either by on electronic device 10, skin analysis device 20, or separate therefrom. Each may take, or be part of taking, multiple skin analysis actions, skin analyses, skin analysis calibrations and skin analysis measurements.

(h) Skin analysis/analyses: one or more analyses of one or more skin characteristics.

(i) Skin analysis action: an action that leads to or results in some portion of skin analysis occurring, such as skin analysis measurements, exemplary skin analysis actions including taking a picture, reading a moisture sensor, testing elasticity via images or recordings, and the like.

(j) Skin analysis calibrations: calibrating one or more aspects of the skin analysis device and/or the electronic device, to allow accurate skin analyses, exemplary skin analysis calibrations including light normalizing for exposure and color temperature (where both may be accomplished using a transformation function for color correction)

(k) Skin analysis device: the device, according to aspects of the present invention, that is removably attachable to an electronic device 10.

(l) Skin analysis measurements: measurements of one or more skin characteristics, including acquiring moisture readings, images for lines/wrinkles/pores, elasticity readings, skin color, and the like, any of which may be represented as 'scores'—either absolute, relative or averages—ie a pore score, a relative line score, a color, etc.

(m) Skin analysis processings: processing of one or skin analysis measurements, such as by performing image processing on an image.

(n) Skin analysis recommendations: using one or more results of one or more skin analyses, and characteristics of one or more skin care products, to recommend an appropriate skin care product for a user.

(o) Skin care products: products that assist with one or more skin care characteristics, such as moisturizers, wrinkle creams, cosmetics (such as foundation and blush), and the like.

(p) Skin care product manufacturers: makers, manufacturers, distributors, brands and brand owners of skin care products.

(q) Skin care product characteristics: attributes of a particular skin product, which may include a product's color, moisturizing ability, line reducing ability, and the like.

(r) Skin care updates: these may include information relevant to skin care that may come from external sources. For example, weather (clouds, sun, high UV, snow) may come from weather sources (not shown, but known to those in the art).

(s) Skin characteristic: characteristics of skin or body part, such as pores, spots, sensitivity (which may use polarized or other light spectrum to show blood vessels that are close to the surface of skin, which may result in 'redder' images, lines, elasticity, moisture, oil, acne, and skin color.

(t) User/human user/subject, person: the person using the skin analysis device and/or who is the subject of the skin characteristic sample, as the case dictates.

(u) User referrer: the entity that causes the user to begin using system 1—such as by encouraging a download of the app (as may be tracked by app download techniques) or by distributing a skin analysis device (as may be tracked using a skin analysis device identifier).

FIG. 1 illustrates aspects of a system 1 with an exemplary electronic device 10 and skin analysis device 20*a* that are able to communicate, via network 100, with skin analysis server 200 ("SAS"), one or more skin care product manufacturers/owners ("product owner") 300 and one or more e-commerce vendors/sites ("vendor") 400.

System

System 1 may allow a user to measure and obtain/collect, store, disseminate, track and act on or use various skin characteristics and samples.

Measuring and obtaining may mean collecting data at one or more times (each a skin characteristic sample) using one or more skin characteristic measurement devices, with or without aid from one or more skin characteristic assisters. Electronic device 10 may have one or more skin characteristic measurement devices (such as camera 12) and one or more skin characteristic assisters (such as vibration motor). Skin analysis device 20 may also have one or more skin characteristic measurement devices (such as moisture sensor 36) and one or more skin characteristic assisters (such as lens 34 or)

Storing may mean local or remote storage of one more skin characteristic samples either for a particular user or for a larger group of users.

Tracking may allow a user to compare themselves to their own prior skin characteristic samples (ie "is my skin more moist than it was a week ago") or to others' skin characteristics samples (ie "is my skin oilier than other people who may be comparable to me").

Acting may mean a user purchases a foundation that matches the color of their skin for the light they are going to be seen in, purchasing a recommended moisturizer and using it, or visiting a doctor to examine concerning spots on their skin.

All of such may be as more thoroughly described herein. All of such may occur between devices, as described herein, which may be connected via one or more networks 100 of varying types and arrangements.

Skin Analysis Server 200

SAS 200 may be a server that stores and processes skin characteristic measurement or sample, as described herein. SAS 200 may be any combination of web servers, applications servers, and database servers, as would be known to those of skill in the art. Each of such servers may comprise typical server components including processors, volatile and non-volatile memory storage devices and software instructions executable thereon. SAS 200 may be central point of communication for app 18 to perform the functionality described herein, including exchanging skin analysis measurement samples, product recommendations, e-commerce capabilities, and the like. Of course skin characteristic application 18 may perform these, alone or in combination with SAS 200, as well.

SAS 200 may include a database server that receives and stores all skin characteristic samples from all users into a user profile for each registered user and guest user. These may be received from one or more electronic devices 10, though app 18 may be configurable to store skin characteristic samples locally only (though that may preclude some of the results information based on population and demographic comparisons).

SAS 200 (and/or app 18) may share user profiles (and any skin characteristic samples received therefrom) with the user referrer, for example when a user profile includes a user referrer. This may be via providing user profiles to a server of a product owner, for example.

SAS 200 may provide various analysis functionality as described herein (such as computing histograms of comparisons with a user's historical scores or of comparisons with peers), and may provide various display functionality as described herein (such as providing websites that may present various analysis, provide links or functional links for other websites to access and display such results, and the like).

Product Owner 300

Product owners 300 may be entities, as defined above with respect to interests in skin care products, and may also have one or more product owner servers including web servers, applications servers, and database servers, as would be known to those of skill in the art. Each of such servers may comprise typical server components including processors, volatile and non-volatile memory storage devices and software executable thereon. Product owner 300 may be a point of communication for app 18 (directly, or via SAS 200) for skin analysis measurement samples (such as those obtained via a user that was provided skin analysis device 20 by such product owner 300) and for storage and execution of product recommendation algorithms. For example, one or more generic product recommendation algorithms may be stored and owned by SAS 200 for each product recommendation type, and product owners may own and implement their own proprietary product recommendation algorithms (for example with product owner 300 receiving the required data to perform the product recommendation algorithm, and returning the recommended product). Product owners 300 may also offer e-commerce services directly, may suggest vendors such as Amazon™ (separately or with the recommended products) or may be agnostic about how a user may purchase a recommended product.

E-Commerce Vendors 400

Vendors 400 may provide one or more e-commerce websites or screens (separate from or embedded in app 18, as screens on app 18, for example) that facilitate business or commercial transactions involving the transfer of information over network 100 (such as the Internet). Types of e-commerce sites include but are not limited to: retail sites, auctions sites, and business-to-business sites. Exemplary vendors 400 that may facilitate the purchase of skin care products may include Amazon™, eBay™, and Overstock™. Of course product owners 300 may have their own e-commerce sites as part of their general websites, or SAS 200 may be such a vendor.

Electronic Device

Electronic device 10 may be a mobile phone such as an iPhone™, such as a 6 or 6s. Electronic device 10 may have one more components thereof, such as camera 12, and other components as are common for such devices, such as flash 8 for camera 12 power and volume buttons, a motor to cause vibration ("vibration motor", interior to electronic device 10), screens, processors, storage/memory, and the like. Some of such components may have visual or physical aspects thereto, that may be visible or present on the exterior surface of electronic device 10 ("visible components"). Other components may be internal to electronic device 10, such as GPS transceivers ("internal components") but may have requirements for external surfaces of electronic device 10 to function properly (such as not blocking GPS or other wireless signals).

Electronic device 10 may comprise expensive and powerful components (including but not limited to processors, storage/memory, camera 12 and the like). However such components may not be suited to be skin characteristic measurement devices, or skin characteristic measurement assisters, without other skin characteristic measurement devices or skin characteristic measurement assisters. For example, camera 12 may have good resolution but may not have adequate traits (such as optical zoom or magnification) to enable capturing images that are suitable for skin characteristics and skin characteristic samples. Hence, as described herein, skin characteristic measurement assisters (on skin analysis device 20 and/or electronic device 10) may be employed, and other skin characteristic measurement devices may be employed).

Electronic device 10 may have software located thereon (such as an 'app') as is known, that may be obtained and installed from an 'app store'. The app according to an embodiment of the present invention may be accessed on electronic device 10 to perform functionality as described herein. The app may also be able to access storage located on electronic device 10, such as to store data, as described herein. The app may also be able to perform communications between electronic device 10 and skin analysis device 20, and network 100 (and hence with SAS 200, product owners 300 and vendors 400.

Electronic device 10 may also have an operating system that provides access to various application programming interfaces ("API"). Such API allow apps on electronic device 10 to 'call' the API and thus access various functionality of electronic device 10 (such as camera 12, controlling a vibration motor, turning on an electronic device light source such as flash 8 or controlling its operation when performing skin care actions, and the like).

Electronic device 10 may have one or more apps 18 (also referred to as skin characteristic applications) installed thereon. App 18 may perform various functionality noted herein, and may be a human user's primary way to interact with electronic device 10 (in terms of accessing functions described herein) and skin analysis device 20. App 18 may be able to access various features and components of electronic device 10. In particular, app 18 may receive inputs from users, and provide activation signals to skin analysis device 20 (for example to take a moisture sensor reading, turn on light sources, and the like).

Electronic device 10 may have an owner/user and may have one more guest users.

Skin Analysis Device 20*a*

Exemplary skin analysis device 20*a* may be one embodiment of skin analysis device 20. Skin analysis device 20*a* may comprise exemplary enclosure 22*a* and sleeve 24*a*, both of which may comprise additional components as described herein. Sleeve 24*a* may be introduced and removably attached to enclosure 22*a*, such as by introducing them together by moving sleeve 24*a* along attachment line 6.

Skin analysis device 20*a* may be introduced and removably attached to electronic device 10, such as by snapping skin analysis device 20*a* onto the back of electronic device 10, following securement lines 2/4. It is to be understood that the shape of skin analysis device 20, and in particular of enclosure 30, may be altered so as to allow attachment to various electronic devices 20 (such as iPhones™, iPads™, various Android™ phones, personal computers, and the like) in various manners (such as by snapping on as portions of enclosure 30 can snuggly attach to protrusions or edges of electronic device 10, allowing electronic device 10 to slide into an electronic device aperture 48). The shape of enclosure 22, or other aspects of skin analysis device 20 as necessary, can easily change to accommodate attachment to various electronic devices 10.

Enclosure 5022, and other aspects of skin analysis device 20 as necessary, can also be altered so as to not block or disrupt the functioning of electronic device 10. By way of example, visible components may include volume controls, power on or wake up buttons, camera 12, flash 8, and the like, and may be exposed via component apertures 46 if such components would have been covered or affected by skin analysis device 20 when attached to electronic device 10. It is also to be understood that the shape of enclosure 50, and other aspects of skin analysis device 20, can easily change to accommodate exposing various visible components, or facilitating the operation of internal components, of various electronic devices In one embodiment, as shown in FIG. 1, sleeve 24*a* may comprise several components of skin analysis device 20, such as lens, color calibrator, light source board, diffuser, moisture sensor, and the like (all largely as described herein but not visible in FIG. 1) and may be removably detachable from enclosure 22*a*. In other embodiments various components of skin analysis device 20 may be separable from other components, such as to create a stand-alone color calibrator as described herein (for example, with one or more of sleeve 24, calibration ring 84, optionally one or more light sources 72/74, optionally with diffuser 38, and a contact ring 28 comprising the stand-alone color calibrator 80.

As shown in FIG. 1, skin analysis device 20 may be located at an upper end 16 of the back side 14 of electronic device 10 and may therefore cover a top portion of the back side of electronic device 10, such as no more than a third of the vertical height of electronic device 10—though the size of such upper portion can be altered as required. Again as shown in FIG. 1, skin analysis device 20 may attach to electronic device 10 such that very little of the front side of the electronic device 10 is blocked.

Figure 2:
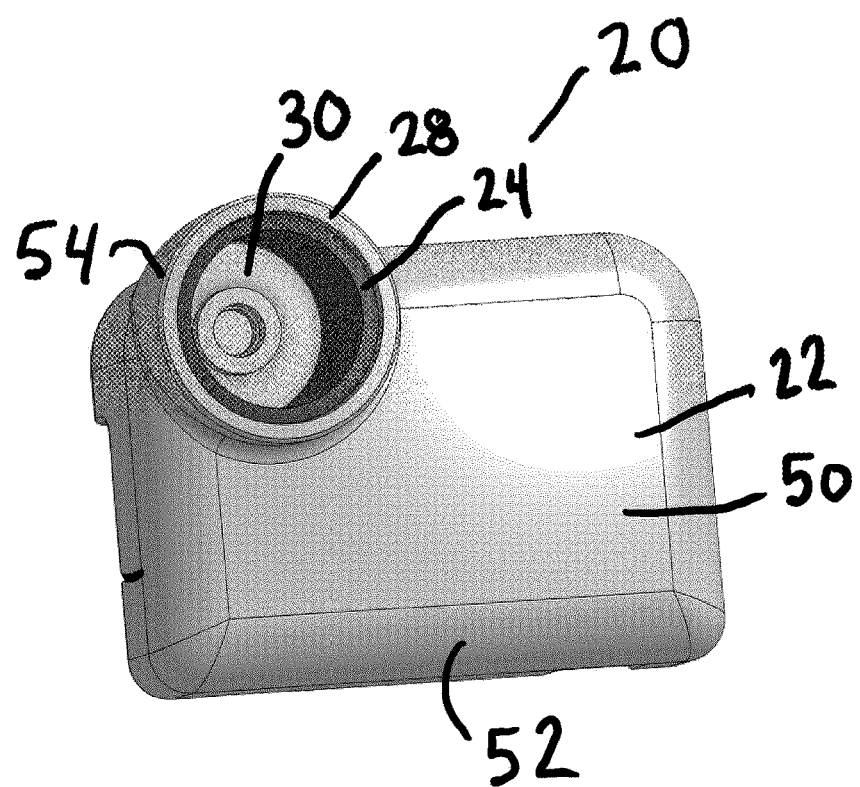
FIGS. 2 and 3 illustrate front views of an exemplary skin analysis device according to an embodiment of the present invention.
Figure 3:
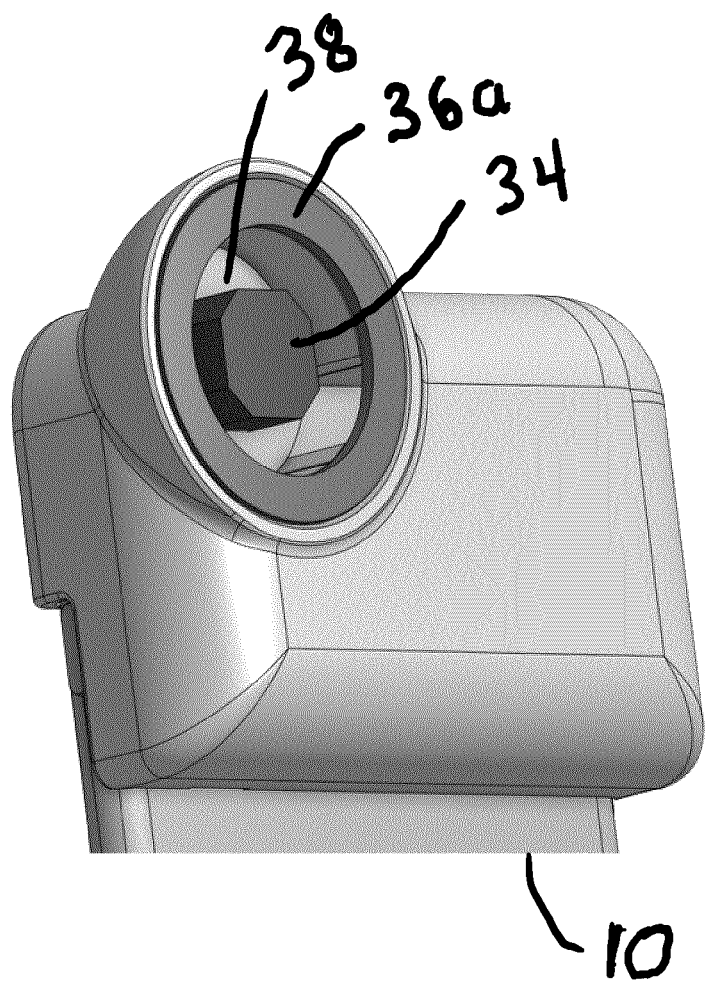
Figure 4A:
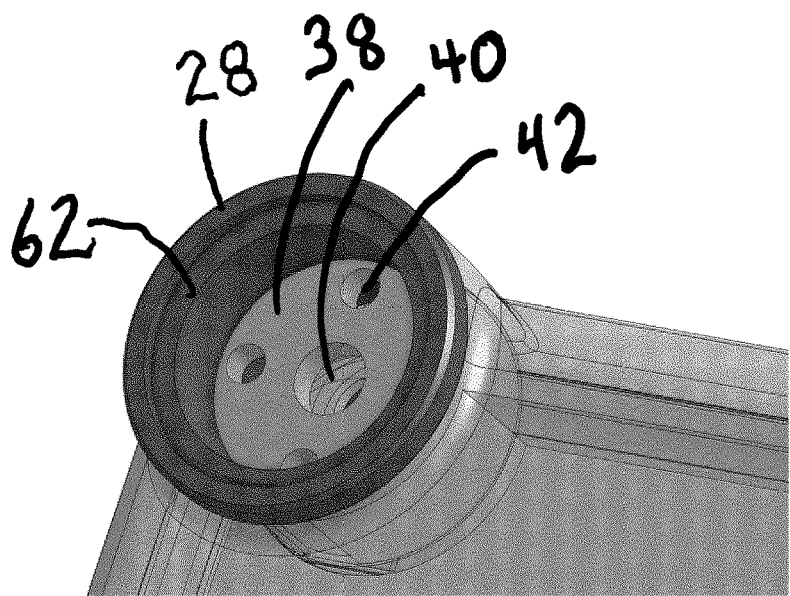
FIGS. 4a-c and 5 illustrate aspects of a sleeve assembly of a skin analysis device according to an embodiment of the invention.
Figure 4B:
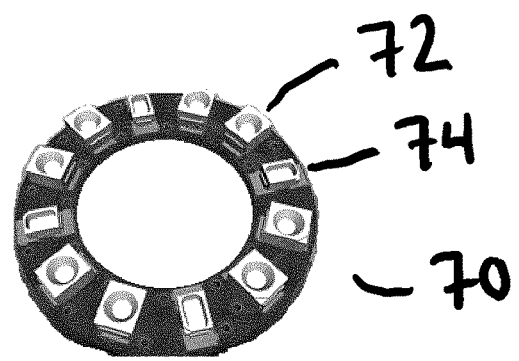
Figure 4C:
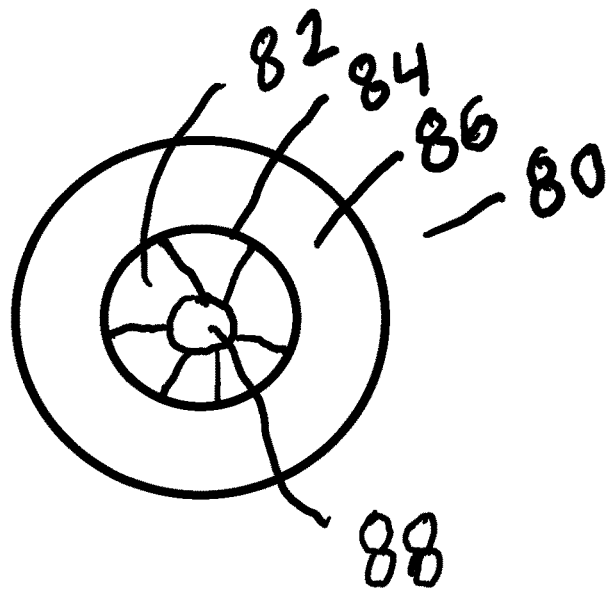
Figure 5:
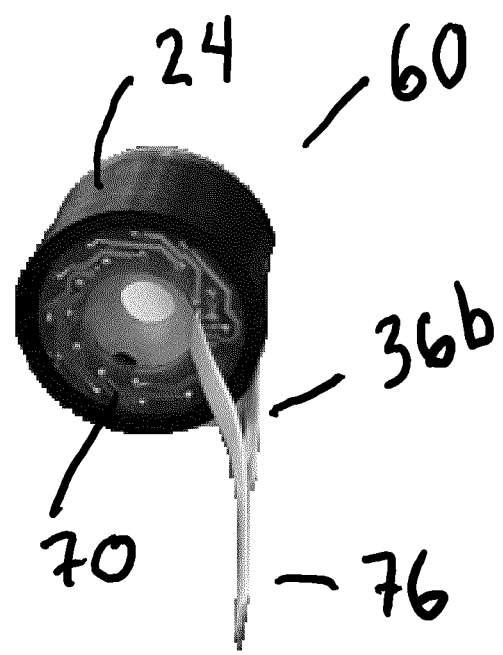
Figure 6:
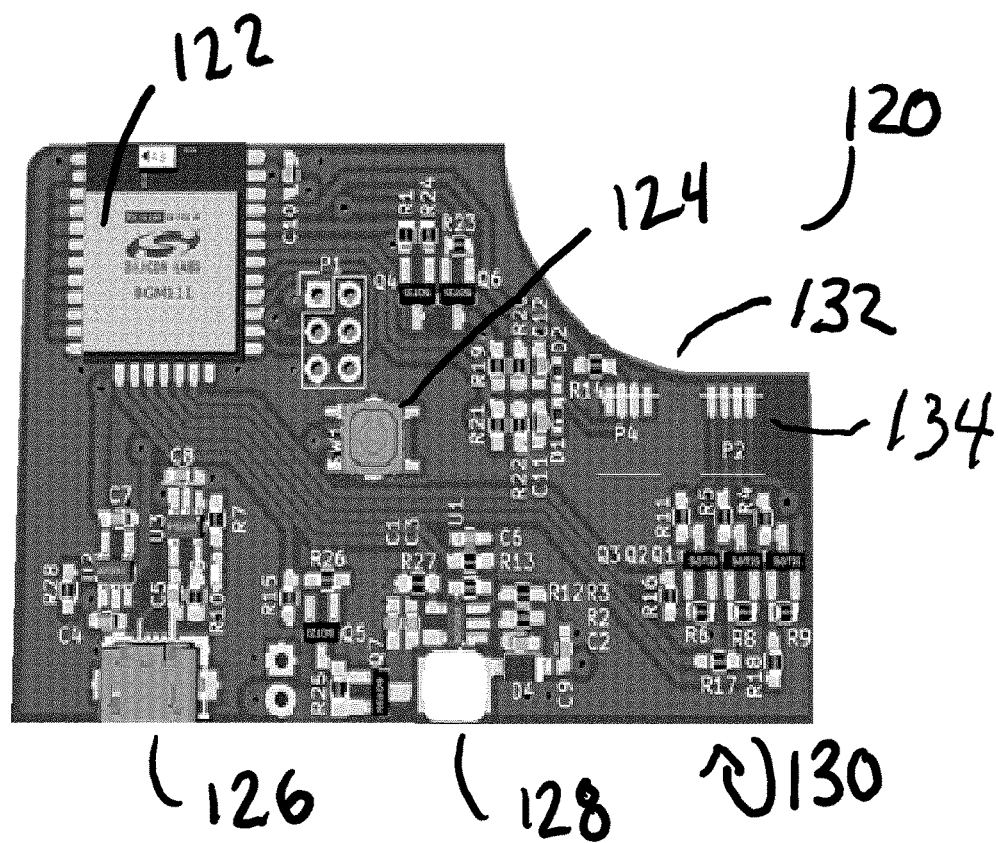
FIG. 6 illustrates a skin analysis device circuit board of a skin analysis device according to an embodiment of the invention.
Figure 7:
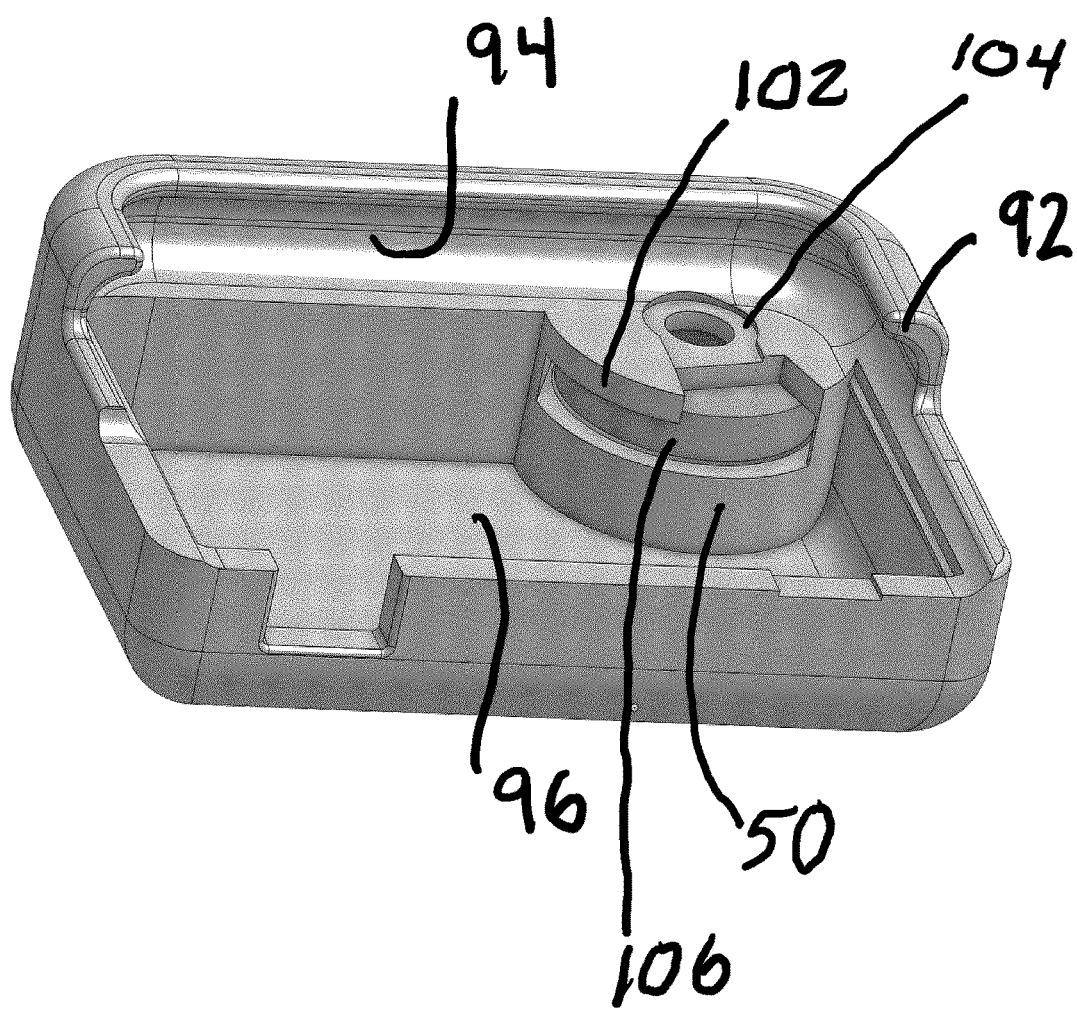
FIGS. 7 and 8 illustrate rear views of an exemplary skin analysis device according to an embodiment of the present invention
Figure 8:
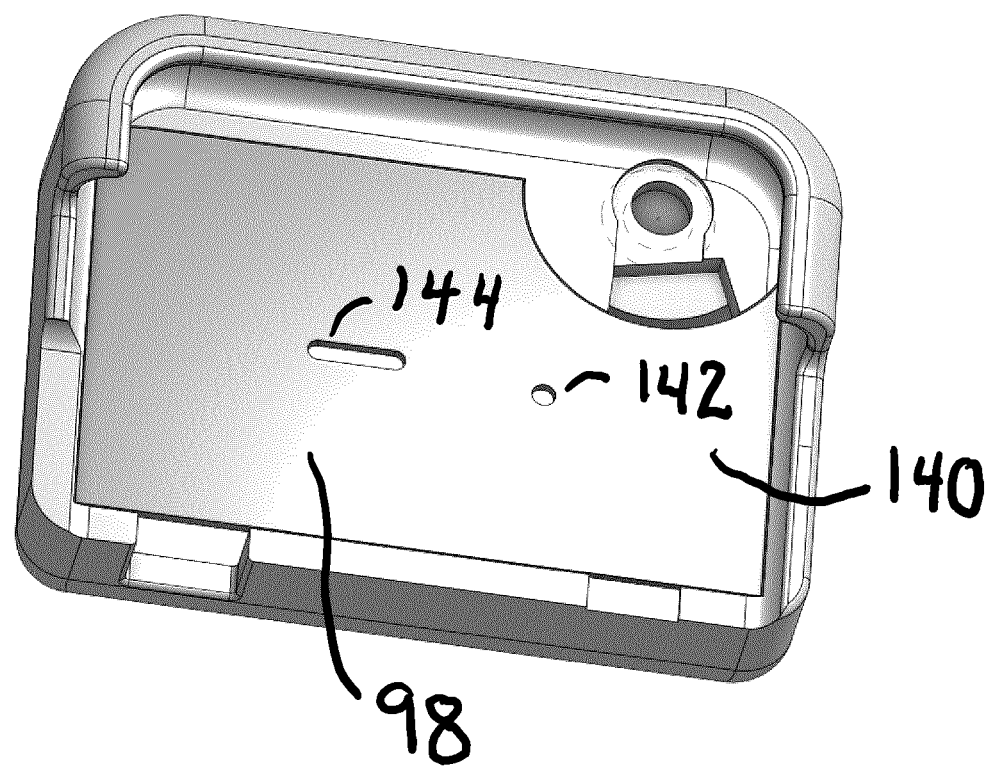

FIGS. 2 and 3 illustrate front views, and FIGS. 7 and 8 illustrate rear views, of an exemplary skin analysis device 20 according to an embodiment of the present invention. Skin analysis device 20 generally comprises enclosure 50 comprising enclosure body 52, cylindrical sleeve assembly aperture 54, board housing 96 and electronic device housing 98 that further comprises top housing 94 and side edges 92, both board housing and electronic device housing 98 working in connection with lid 140 to house PCB 120 and electronic device 10 respectively, lens 34, cylindrical sleeve assembly 60 comprising cylindrical sleeve 24, moisture sensor 36*a* with moisture sensor leads 36*b*, light source board 70 comprising first light source 72, second light source 74 and light source leads 76, diffuser 38 comprising light source aperture 42 and camera lens aperture 40, and color calibration ring 80 comprising adhesive strip 86, calibration ring 84 having one or more color quadrants 82, skin analysis device circuit board (PCB) 120 comprising sleeve cutout 132, processor (which may also include a Bluetooth™ transceiver) 122, connector 126, charge indicator 128, reset button 124 and battery 130 (not shown, on the reverse side of PCB 120), and lid 140 comprising reset aperture 144 and charging aperture 142.

Enclosure

Enclosure 50 comprises an enclosure body 52, configured to be removably connected to electronic device 10, and a cylindrical sleeve assembly aperture 54 configured to receive a cylindrical sleeve assembly 60 and be disposed in front of camera 12 of the electronic device 10 when the skin analysis device 20 is attached to electronic device 10. When attached enclosure or other portions of skin analysis device 20 may cover flash 8 so that any light that is part of images of a user's skin come from light source 70.

Cylindrical sleeve assembly aperture 54, also known as sleeve housing 54, may further comprise base plate 102, lens plate 104 and wire aperture 106. Base plate 102 may be a surface, proximate to electronic device 10 and optionally forming a portion of electronic device housing 98. Base plate 102 may be a surface to which lens 34 and/or sleeve assembly 60, are bonded and/or rests on when inserted in sleeve assembly aperture 54. Lens plate 104 may be a portion of base plate 102 that conforms to the shape of lens 34 to facilitate lens resting in the proper position when skin analysis device 20 is attached to electronic device 10. Wire aperture 106 may be an opening in sleeve housing 54 that is configured to allow electrical connections from one or more of moisture sensor 36*a* (such as moisture sensor leads 36*b*) and light source assembly (such as leads 76) to be attached to PCB 120.

Sleeve housing 54 may further comprise a contact surface 28 that may be substantially in contact with the subject when skin analysis occurs. Contact surface 28 may be of a material that is comfortable for a user, such as plastic or rubber and may be integral with enclosure 50 or may be a separate component that is connectable thereto.

Sleeve housing 54 may further comprise one or more lips or shelves 62. Shelf 62 may be a portion, optionally cylindrical, of sleeve housing 54 on which moisture sensor 36 and/or color calibrator are attached. Lips 62 may be radially interior from contact surface 28 such that contact surface largely envelopes lips 62.

Electronic device 10 may be slide into electronic device housing 98 such that electronic device 10 is in contact with lid 140 and is kept in place by lid 140, top housing 94 and side edges 92. Such connection may be tight enough, for example as a result of the relative dimensions of electronic device housing 98 and/or material properties of enclosure 50 and electronic device 10, that removal of skin analysis device 20 from electronic device 10 is unlikely to occur with a user attempting to do so.

Enclosure 50 has a front surface 22 on which advertising or other information may be printed, stuck or otherwise located.

Lid

Lid 140 may be slideably inserted, or placed, inside board housing 96 to protect PCB from the environment outside of skin analysis device 20. Lid 140 may be shaped to fit in board housing 96 and otherwise fit with the internal layout of PCB 120 (hence reset aperture 144 and charging aperture 142 that allow access to reset button 124, and charging button 128, respectively). Lid 140, when inserted, may form part of electronic device housing 98.

Lens

Skin analysis device 20 further comprises lens 34, attachedly inserted in the cylindrical sleeve assembly aperture 54, radially closer to the camera than a first light source. Lens 34 may have a working distance to the skin/surface of 16 mm and a working distance to camera 12 lens of 2 mm. Lens 34 may be glass coated. There may also be one or more polarizers (which may be thin and tinted sheets that polarize one or more light sources that go through polarizer and window to assist with sensitivity analysis, and which may be located between lens 34 and the skin. Lens 34 may be a magnification lens that has a magnification factor as appropriate for the skin surface being imaged (for example a 30× lens 34 for skin analysis and a different magnification for hair analysis).

Sleeve Assembly

Cylindrical sleeve assembly 60, may be attachedly inserted in cylindrical sleeve assembly aperture 54, and comprising a cylindrical sleeve 24, moisture sensor 36 disposed on or in the cylindrical sleeve assembly 60 and optionally located at a axially remote end of the sleeve from the camera, such that moisture sensor 36 can measure moisture qualities of a surface of the human user when the skin analysis device 20 is in a measuring mode, and a light diffuser assembly, that diffuses light from a first light source located thereon, disposed in front of the camera when the skin analysis device is attached to the electronic device, on an axially proximate end of the sleeve from camera 12.

Cylindrical Sleeve

Sleeve 24 may be a cylinder that is sized so as to be insertable into housing 50. Sleeve 24 may rest on base plate 102 when attached to enclosure substantially black on the inside. Sleeve 24 may have an interior surface and an exterior surface. Interior surface of sleeve 24 may be light absorbing, such as a black color, so that the nature of the light that is directed at the subject (such as a user's skin) is known.

Moisture Sensor

Moisture sensor 36 may comprise sensor 36a and sensor leads 36b. Moisture sensor 36 may measure the moisture content of the skin and provide such measurement to skin analysis device processor 122. Moisture sensor 36 may be capacitive or resistive. In one embodiment moisture sensor 36 is capacitive and comprises two circular/cylindrical electrodes, having track thicknesses of 0.3-1 mm, with a gap therebetween of 0.1-1.5 mm. Moisture sensor 36 may be disposed on, and attached to, lips 62 of sleeve 24 and may be shaped such that they do not interfere with camera 12 (and thus may be located radially exterior to the inner/inside surface of sleeve 24 through which camera 12 may capture an image.

In testing a moisture sensor with 0.9 mm tracks and a gap of 0.1 mm was found to produce acceptably reliable and repeatable capacitance values for various readings (skin on face, skin on arm, and the like) and a good range of capacitances such that several gradations or degrees of moisture could be attributed to the subject skin or surface.

Moisture sensor 36 may be in communication with a skin analysis device processor via moisture sensor leads 36b that may travel along sleeve aperture 54, through wire aperture 106 and be connected to PCB 120.

When in use, skin analysis device 20, and in particular moisture sensor 36 and contact ring 28 may be touching a user's face or other surface. The amount of pressure applied to skin analysis device 20 to touch a user's face, or be pressed into contact therewith, can affect moisture sensor 36 readings, in a measurable and predictable way. However it may be difficult to determine how hard a user is pushing during a given use. To combat this a sensor focus distance calibration may be undertaken. This may involve asking a user to push the device hard, using forceful pressure, and allow the autofocus to determine a first lens travel distance as it takes a first moisture reading, and then asking the user to push the skin analysis device lightly, using light pressure, and allow the autofocus to determine a second lens travel distance as it takes a second moisture reading. App 18 may then conduct an interpolation between these values, and calculate the equation that best correlates to a range of focus distances and moisture readings, as described herein. Then each future time a moisture reading, likely using unknown pressure, is taken the future focus distance may be captured, compared to the first lens travel distance and second lens travel distance, to determine a moisture factoring value that can be applied to the moisture reading. Of course such approach may rely on camera 12 being a camera 12 with variable focus distance.

Light Source Board

Light source board 70 may comprise first light source 72, second light source 74 and light source leads 76. Light source board 70 may be in communication with the skin analysis device processor, such as via light source leads 76. Light source board 70 may, in combination with diffuser 38, be referred to as light source assembly.

First light source: A first light source may be light emitting diode (LED) lights, such as via Vishay Semiconductors'™ VLMU3100 (Power SMD LED PLCC-2), which may have known light characteristics (such as luminous intensity, luminous intensity with angular displacement, chromaticity, and the like) which may be published in technical documentation related thereto. The first light source being LED light may mean that such light needs to be diffused so that white spots are not created on an image that is taken. As such, each LED light may be directly behind diffuser 38 and its light may not pass through light source aperture 42. Some LED lights may be configured, with one or more polarizers, to be polarized.

Second light source: A second light source may be ultra-violet (UV) lights, such as via Vishay Semiconductors™ VLMU1610-365-135, which may have known light characteristics (such as luminous intensity, luminous intensity with angular displacement, chromaticity, and the like) which may be published in technical documentation related thereto. The second light source being UV light may mean that such light does not need to be diffused when an image that is taken. As such, each UV light may be directly behind a light source aperture 42, such that the UV light passes through such light source aperture 42. UV lights may be considered an adverse effect device, in that it can be dangerous if used improperly (such as directed into a user's eyes for long periods). As such extra care may be taken in the control of the activation of UV lights, as described herein.

Light source board 70 may specifically feature multiple lights, from multiple light sources, that may be individually controllable and mounted so that the angle of light hitting the surface of the skin is varied. The varied angles may illuminate the skin to reveal specific textures in a 3D type of effect. This may assist in one or more skin analyses, such as by providing a measure of the depth of a line or wrinkle.

In use, because the light spectrum of the one or more light sources (such as first light source and second light source, or any others that may be added) is known, flash 8 may be blocked or disabled (such as via app 18), contact ring 28 may be tight against a user's face (creating a a user contact point where at least a portion of skin analysis device 10 and/or electronic device 10 are proximate to or in contact with a user's skin) and sleeve 24 blocks out external light, the spectrum of light applied to a user's skin can be known. Optionally in combination with color calibrator 80 this may allow one or more color matching functionalities as described herein.

It may be desirable to use light source board 70 (in combination with other components noted herein to keep out other light sources) instead of flash 8, not only so the spectrum of light is known and is consistent (potentially more consistent than from flash 8) but also so that shadows and other anomalies may be eliminated—which could cause difficulty in various processings.

Of course light source board may have any number of light sources, and various other light sources may be used. For example infrared light may be used, which may be able to measure skin temperature and hence be used for different dermatological assessments.

Diffuser

Diffuser 38 may be a component that is shaped and sized to fit inside sleeve 24, and thus may be a circle or cylinder. Diffuser may be made of any material of any color provided that such has the diffusing properties required based on the light source(s) that are to be diffused. In one example such diffuser 38 may be a white plastic. Diffuser may comprise one or more light source apertures 42, arranged to allow the desired light through from light source board, and camera lens aperture 40 to allow camera 12 to function with lens 34 to take images.

Color Calibrator

Color calibrator 80 may be an exemplary passive skin characteristic measurement assister. Color calibrator 80 may be configured such that when camera 12 takes an image, color calibrator 80, or at least a portion of calibration ring 84, having at least one color quadrant 82, may be part of the image, for example a radial portion of the field of view of camera 12.

Color calibrator 80 may comprise adhesive strip 86 that may assist in sticking color calibrator 80 to skin analysis device 20, such as by folding adhesive strip 86 so that it is inserted axially inside sleeve aperture 54 and calibration ring 84 is at least partially in the field of view of camera 12 (such as being the radially exterior portion of the field of view— thus creating both a human user portion and a color calibration portion when an image of a human user is taken). Of course color calibrator 80 may have a center aperture 88 that is sized such that camera 12 can take a picture, through lens 34 as described herein, and still take a large enough sample of a user's skin to be effective. Color quadrants 82 may include any number of colors of known properties. In one embodiment there may be a sole color quadrant, with a sole known color, being gray with an RGB value of 122/122/121. As such, when an image is taken by camera 12 the colors of the user's skin can be adjusted based on the adjustments to the colors of color quadrants 82 as compared to their known colors (as further described herein).

When combined with other components, color calibrator 80 may form a color calibrator assembly. Color calibrator assembly may essentially keep all light, not coming from flash 8, out of an image taken by camera 12.

Such color calibrator assembly may include color calibrator 80, sleeve 24, and skin contact ring 28. In such a configuration color calibrator assembly may remain a passive skin characteristic measurement assister. In another embodiment a color calibrator assembly may further comprise light source board and/or diffuser 38, which may make it a more effective and flexible color calibrator assembly and make it an active skin characteristic measurement assister. As an active characteristic measurement assister color calibrator assembly may require processor 24 or another way to control light source board 70.

Configuration color calibrator assembly may be attached to electronic device 10 using skin analysis device 20, or portions thereof, or may have a simple attachment mechanism ("color calibrator assembly attachment") such as an adhesive ring on the end of sleeve 24, or a simple mechanical element that snaps or hooks onto electronic device 10 at an attachment point. Color calibrator assembly attachment may allow flash 8 to direct light into color calibrator assembly attachment, particularly when being used as a passive characteristic measurement assister.

Although described herein as a component that may be part of skin analysis device 20, color calibrator may also be part of a stand-alone device that attaches to electronic device 10.

PCB

Components

PCB 120 may comprise comprising sleeve cutout 132, processor (which may also include a Bluetooth™ transceiver) 122, connector 126, charge indicator 128, reset button 124, battery 130 (not shown, on the reverse side of PCB 120) and one or more I/O connections 134.

PCB 120 may be a typically constructed circuit board, with standard connections between components. PCB 120 may be shaped so as to be insertable into board housing 96, including having sleeve cutout 132 to fit around sleeve housing 54.

Connector 126 may allow PCB to be connected to a charging and/or data transfer wire, such as micro or mini USB, as is known in the art. Charge indicator 128 may simply indicate that battery 130 is charging. Reset button 124 may allow PCB 120, and processor 122 in particular, to be reset.

PCB further comprises battery 130 (on reverse of board 120), to provide power to PCB 120, and hence power attached components (such as moisture sensor 36 and light source board 70). Battery 130 may be charged by plugging into connector 126, which may be a micro or mini USB port.

PCB 120, and more particularly processor 132, is in communication with electronic device 10 (for example using Bluetooth transceiver that may be part of processor 132 or via another wired or wireless connection), and moisture sensor 36 and light source board 70, for example via I/O connections 134.

Processor 132 may be a microprocessor that is capable of varied and complex functioning—as described herein— including assisting in obtaining skin analysis samples (such as by controlling the functioning of moisture sensor 36 and light source board 120) and processing data (such as skin analysis samples), communicating (or controlling communications). Components of skin analysis device that communicate with or are capable of being controlled by processor 132 may be considered active components. Processor 132 may comprise a Bluetooth transceiver, to enable it to communicate with substantially any Bluetooth device, but preferably with at least electronic device 10 so as to facilitate the functionality described herein.

Processor 132 may be a Bluetooth integrated microprocessor from Silicon Labs™ (BGM111) microprocessor but may have custom firmware.

Custom firmware may comprise largely off-the shelf software (OTSS) instructions to control typical features. However, custom software instructions may be written to enable the functionality described herein, and improve deficiencies in typical firmware. In one embodiment custom firmware may simply be written to remove unnecessary code that results in slower responsiveness of processor 132.

Operation

Processor 132 may perform at least the following operations:

(a) With respect to light source board 70: control turning on and off any of the light sources or individual lights thereof, for a specified duration.

(b) With respect to moisture sensor 36: control the taking of a reading and receiving the reading.

(c) With respect to the functioning of a Bluetooth transceiver (embedded in processor 132 or separate therefrom): advertise its Bluetooth signal to connect to electronic device 10, communicate via Bluetooth as required to establish and maintain a connection and perform functionality as described herein.

(d) With respect to electronic device 10:
  (i) receive signals from electronic device 10 to control one or more of light source board 70 or moisture sensor 36 (for example receiving sample taking signals from electronic device 10 that indicates that samples will be taken),
  (ii) provide signals and or skin characteristic samples to electronic device 10, such as moisture sensor readings and light information (such as spectral properties of one or more light sources that were on when an image was taken, and the like).
(e) With respect to, and related to battery 130: Monitor battery voltage, shut off one or more components of PCB 120 if battery 130 voltage drops below a set and configurable threshold, monitor charging of battery 130.

Skin Analysis Device—Assembly

Figure 9:
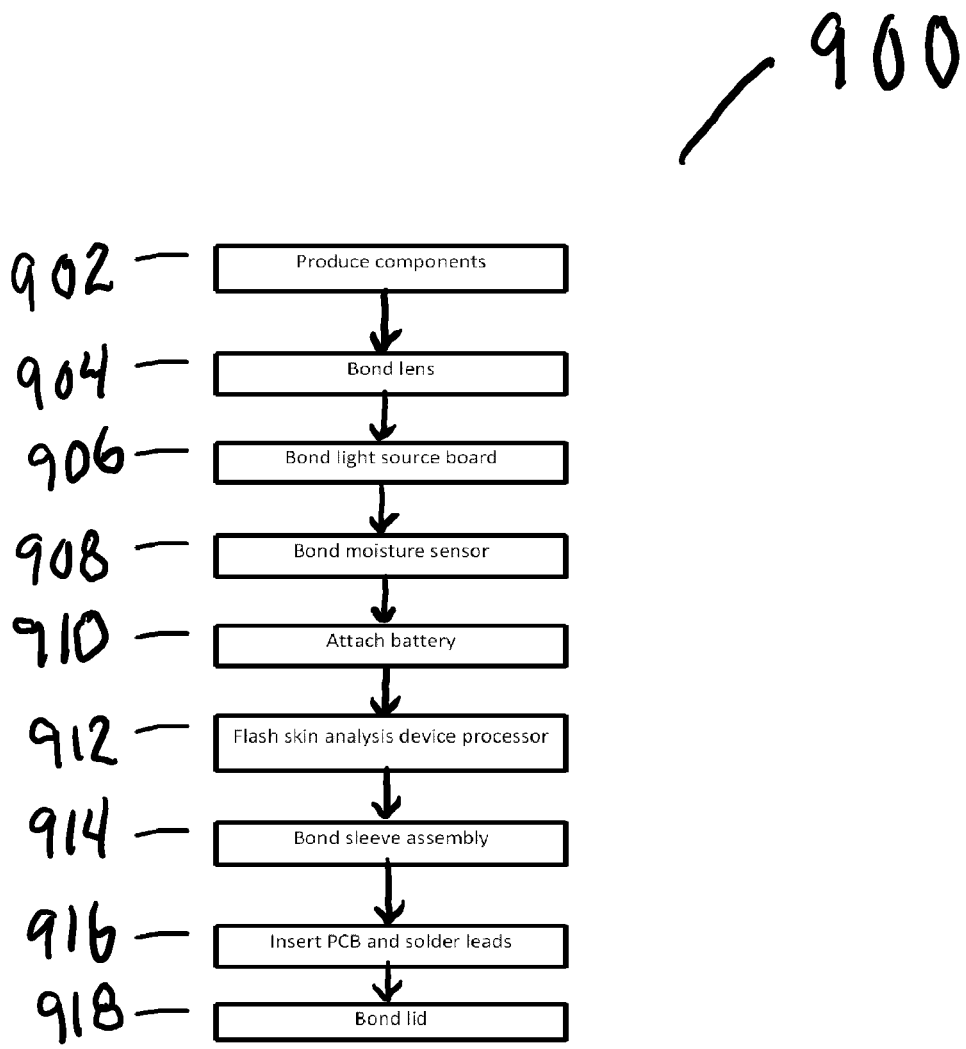
FIG. 9 is a method for assembly of an exemplary skin analysis device according to an aspect of the present invention.

FIG. 9 is a method 900 for assembly of a skin analysis device 20 according to an aspect of the present invention.

Method 900 begins at 902 where various components are produced, such as via a 3d printer. Such printed components may comprise enclosure 20, sleeve 24, and enclosure lid 140. As part of such producing/printing, such printed components may be trimmed, to remove support materials.

At step 904 lens 34 may be bonded in enclosure 24. This may be by gluing lens 34 onto base plate 102 and into lens plate 104.

At step 906 light source board 70 may be bonded on one end of sleeve 24. The end having light source board 70 may be the end that is proximate to electronic device 10 ("proximate end"). Bonding may involve gluing light source board 70 to sleeve 24 such that light sources are radially inside sleeve 24 and direct light through sleeve 24 towards the remote end of sleeve 24, as described herein.

At step 908 moisture sensor 36 may be bonded on one end of sleeve 24 (the opposite end from where light source board 70 may be bonded, which may be the end of sleeve 24 away from the electronic device ("remote end"). Bonding may involve gluing light source board 70 to sleeve 24.

At step 910 a battery may be attached to skin analysis device processor board 70 and leads (such as moisture sensor leads 36*b* and light source board leads 76) may be soldered to provide power thereto.

At step 912 processor 122 may be flashed with custom firmware, as described herein.

At step 914 sleeve 24 may be slid into enclosure 50 and bonded thereto, for example by applying glue to inner surfaces of sleeve housing 54.

At step 916 skin analysis device processor board may be inserted into enclosure 50 and wires for light source board 70 and moisture sensor 36 may be soldered to skin analysis device processor board 120.

At step 916 skin analysis device processor board may be inserted into enclosure 22 and wires for light source board 70 and moisture sensor 36 may be soldered to skin analysis device processor board 120.

At step 918 lid 140 may be inserted into enclosure lid aperture 96 and bonded thereto, for example by applying glue thereto. Optionally enclosure lid aperture may be designed such that the connection causes lid 140 to snap into place.

Various tests may then be undertaken, with or without being attached to electronic device 10, to ensure proper functioning of skin analysis device 20, though is may be separate from assembly. Exemplary tests may include:
(a) Lens focus: focusing camera 12, through lens 34, on a test pattern, to ensure that the images taken are sharp.
(b) Bluetooth working: check if the Bluetooth serial number is broadcast.
(c) LEDs functioning: check if light sources can be controlled and operate properly.
(d) Moisture sensor reading check: test moisture sensor 36 in open air and against a moist towel to ensure appropriate values are obtained.

Of course it is to be understood that various methods of assembling skin analysis device 20 may be followed, and various adjustments may be made to method 900.

Figure 10:
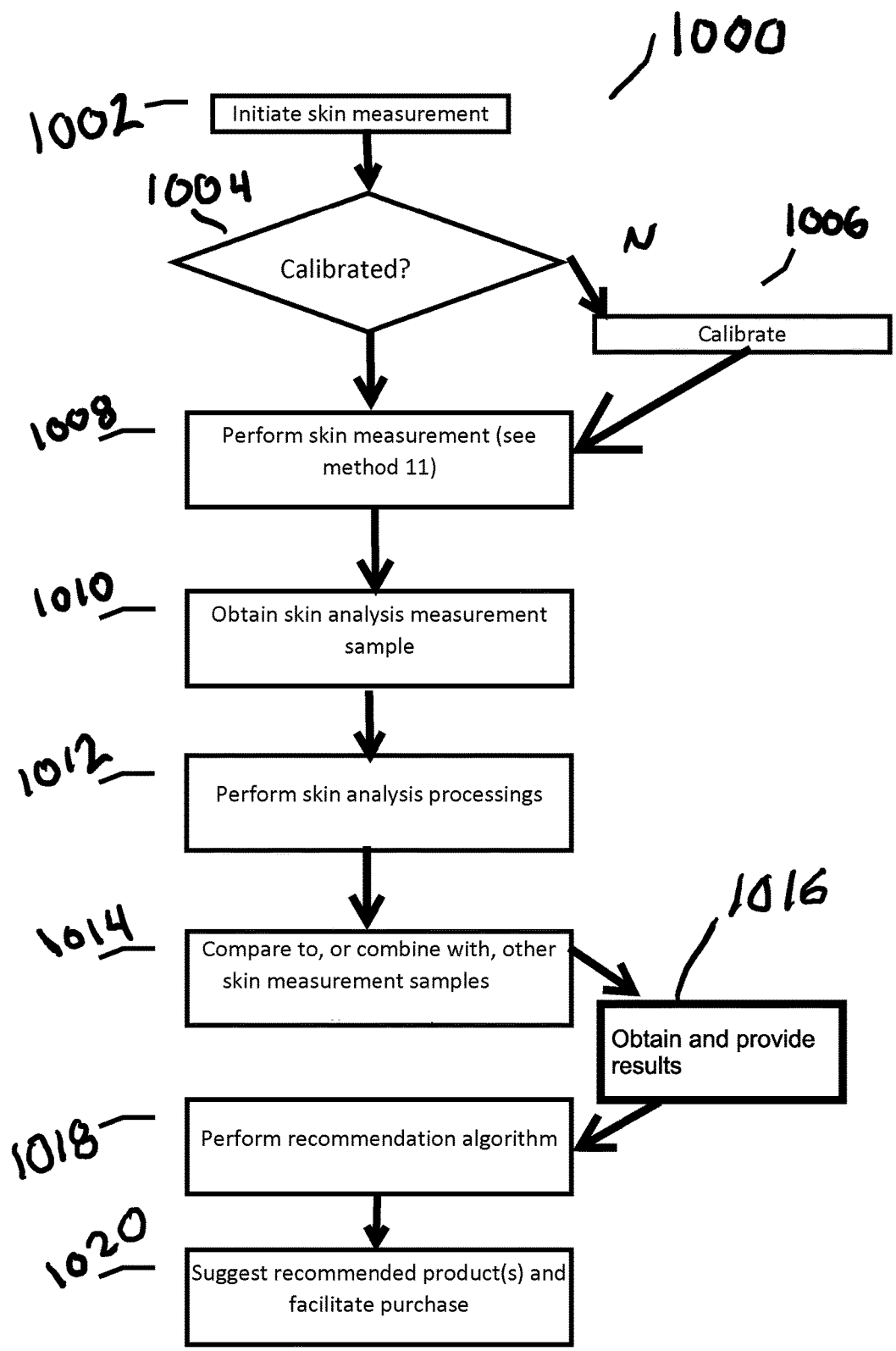
FIG. 10 is a method for use of a skin analysis device according to an aspect of the present invention.

FIG. 10 is a method 1000 for use of a skin analysis device 20 according to an aspect of the present invention.

Method 1000 may be implemented by various elements of system 1, alone or in combination. Parts of method 1000 may be implemented or performed separately, together and in various orders (even if depicted as part of method 1000 and in a particular order). Various portions of method 1000 may be depicted in screenshots 1200*a-m*, 1400*a-d* and 1500*a-b*.

Method 1000 begins at 1002 where a skin measurement is initiated. This may be, for example, via selecting 1202, 1204, 1232 or 1234. Although possible for initiation to occur via skin analysis device 20 or other aspects of system 1, in a typical use initiation is via app 18 and a user thereof. As shown and described herein, initiation may be of one or more skin characteristic measurements, in largely any combination.

At 1004 a query is made whether skin analysis device 20 and electronic device 10 are calibrated. This query may be answered via app 18, for example that may store information or flags that indicate whether one or more calibrations have been done (for example an autofocus based moisture sensor calibration flag that indicates whether such calibration has occurred). Calibrations that are subject to the query may be any and all calibrations or may only be the calibrations that may be required for the skin characteristic measurements that have bene initiated.

If any required calibrations have not occurred then method 1000 proceeds to 1006 where such calibrations are performed. Exemplary calibrations include:
(a) Focus based moisture sensor calibration:
  (i) A user takes a picture when they are lightly touching skin analysis device 20 to their skin (sample A) and then when they are quite firmly touching skin analysis device 20 to their skin (sample B).
  (ii) To take the picture the user is asked to touch the middle of the screen (as a trigger prompting app 18 to control API to instruct camera 12 to take a picture) in the middle of the screen/image, which will tell camera 12 to focus on that spot as its focal point. Camera 12 will then adjust its focus, which will result in the focus distance parameter being a value between 0 and 1 (for at least some electronic devices, though the value range may vary). At the same time moisture sensor 36 will be read to obtain a moisture value.
  (iii) Having taken two values for depth of focus and moisture, it can be determined how much the pressure from the user impacts moisture (a pressure-based moisture adjustment factor). A simple (two point) X vs Y graph can be produced and a line drawn between the two data points. The slope of the line can then be determined, and will be assumed to be the pressure-based moisture adjustment slope for all measurements using the moisture sensor 36 where there are differences in pressure applied.

(iv) Averaging the two depth of focus values also produces an "average pressure" depth of focus value, or average focus distance. Each subsequent moisture sensor reading will be normalized as if the depth of focus had been the average.

(v) In general, this may be accomplished via solving a slope point form equation of the form Y−Y1=m(X−X1), where
   (A) Y is the adjusted future moisture sensor reading;
   (B) Y1 is the future moisture sensor reading;
   (C) m is the pressure-based moisture adjustment slope;
   (D) X is the average focal length; and
   (E) X1 is the future focal length.

(vi) By way of example, sample A may have a moisture level of 1000 and a depth of focus of 0.2. Sample B may have a moisture level of 1500 and a depth of focus of 0.8. The slope of the line is thus 833. The average depth of focus is 0.5.

(vii) Then a new measurement is made (sample C), of a new surface or area of skin (ie an actual sample being collected, calibration having been completed when a slope was determined). Sample C has a depth of focus of 0.3 and a moisture level of 600. Using point-slope form, the moisture level can be adjusted to simulate a depth of focus of 0.5, resulting in an adjusted moisture level of 766.

(viii) This calibration may be done one or more times—for example on a first use of skin analysis device 20, on a first use of skin analysis device 20 with a particular electronic device 10, on a first use for a new user (including a guest user) of electronic device 10.

(b) Image calibration (exposure and color temperature): a transform function is used to scale the RGB value read from one or more known colors on color calibrator 80, to scale it to its target (known) value. The same scaling factor is applied to every pixel in the skin image. This may be as described herein.

If calibrations are not required then method 1000 continues at 1008 where skin measurements occur. For each skin characteristic measurement that is undertaken there may be one or more skin characteristic measurement devices and one or more skin characteristic assisters involved. These may all need to work in unison to properly perform such skin characteristic measurements. In one embodiment the skin characteristic measurements may be based on one or more of a moisture sensor reading and/or image(s) of the user.

Figure 11:
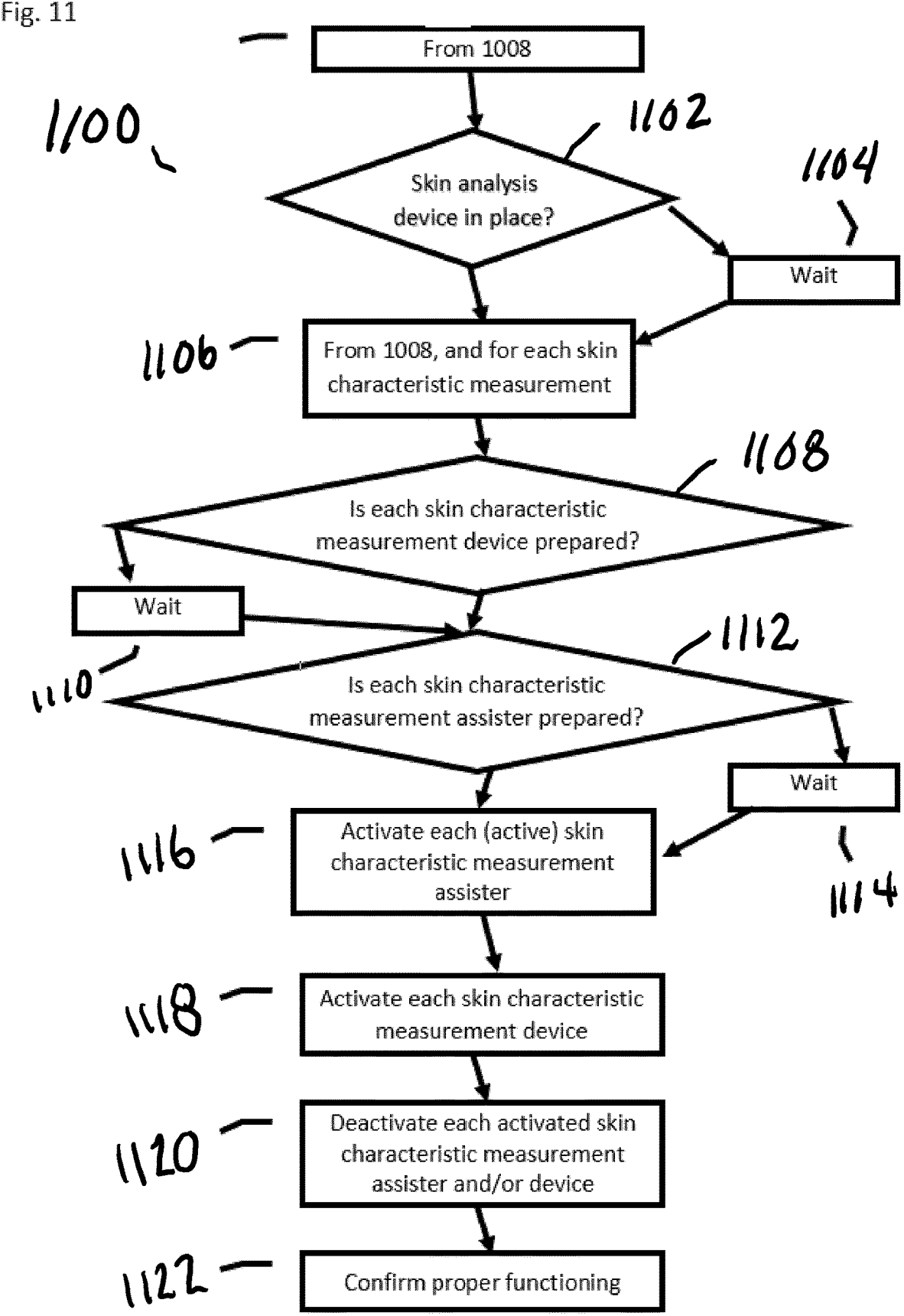
FIG. 11 is a method for performing skin care measurements according to an aspect of the present invention.

Step 1008 may be more fully described in FIG. 11 but but in one simple example the skin characteristic may be a pore analysis and step 1008 may involve:
(a) Electronic device being provided an input to take a picture (for example by a user pushing a button, such as a volume up button), which is received by app 18;
(b) App 18 communicating, via Bluetooth, with processor 122 to have processor 122 turn on first light source 72;
(c) App 18 using the camera API to take a picture at the same time as first light source 72 is on;
(d) App 18 communicating, via Bluetooth, with processor 122 to have processor 122 turn off first light source 72.

Portions of 1008 and FIG. 11 may be performed or initiated using screenshots 1200*b*/1200*d*/1200*e*, for example.

Method 1000 then continues to 1010 where the skin analysis measurement sample is obtained. This may involve app 18 receiving the image from camera 12 (such as images 1610, 1630, 1650), or receiving a moisture level from moisture sensor 36, which may be received by processor 122 and then communicated to app 18 via, for example, Bluetooth. It is to be understood that generally step 1010 involves getting the captured data, generally unprocessed, from the skin characteristic measurement device(s) to app 18.

Method 1000 then continues to 1012 where processing of the skin characteristic measurement sample may occur (ie one or more skin analysis processings). Of course such skin analysis processings will depend on what skin characteristic measurement(s) were taken. However exemplary skin analysis processings may include various image processing techniques (as described herein and shown in FIGS. 10, 11 and 13) that may take raw images (from camera 12) and apply various techniques thereto.

By way of a few examples, the following skin care processings may be performed:
(a) Lines/wrinkles processings—the following steps are performed:
   (i) The image is converted from RGB to L*ab color space, providing luminance, green-red and blue-yellow color components;
   (ii) Hair elimination—the L*ab image is filtered by removing very dark pixels (if a pixel's luminance value is significantly darker than the average luminance for the image);
   (iii) Apply a high pass filter to remove minor noise without reducing sharpness (as Gaussian Blur would do) or contrast;
   (iv) Convert the image into a black and white image;
   (v) Using a morphological skeleton in order to identify possible structure in darker formations (like possible lines, possible wrinkles and possible pores);
   (vi) Apply a probabilistic Hough Transform which may result in a list of lines filling the vacant spaces after the previous filter(s), such resulting lines may be rendered as white lines into a separate monochromatic black image;
   (vii) Apply an inversion to convert dark to light, and the reverse;
   (viii) Apply a probabilistic Hough transform, for example as a 2nd pass, which results in a list of lines which have a significant chance of being wrinkles in the original image. The list is then filtered by length and the remaining lines are grouped. The resulting line list is used to calculate the score of the original image—where scores may be affected by having different numbers of lines and lines of different characteristics (lengths, widths and the like).
   (ix) Exemplary results may be as shown in image 1640.
(b) Pores processings
   (i) Generally this approach uses edge detection to identify darker areas of the image that are surrounded by lighter pixels. Then a second pass may be performed to eliminate areas larger than, for example 500 micrometers, since these are not likely pores. In more detail:
   (ii) Obtain the image as a pixel matrix (rgb—for example where each pixel has a pixel color, in rgb) and convert it to a grayscale image (each pixel has r=g=b);
   (iii) Create an empty matrix with zeros (0) on each position, of equal width and height with the one from 1);
   (iv) Calculate the mean value of the grayscale matrix:
   (v) Subtract each grayscale matrix element from the mean value to obtain a new matrix.

Figure 12A:
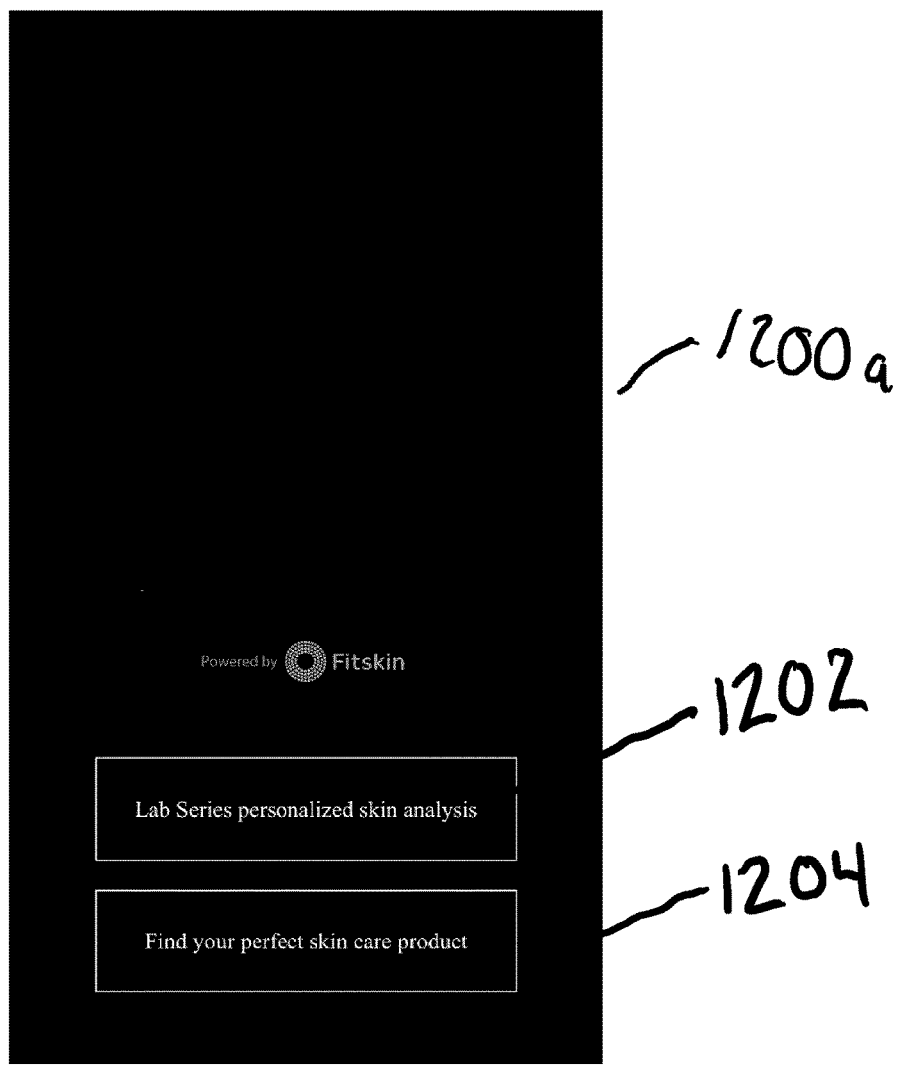
FIGS. 12a-m illustrate screenshots of an app for an electronic device according to an aspect of the present invention.
Figure 12B:
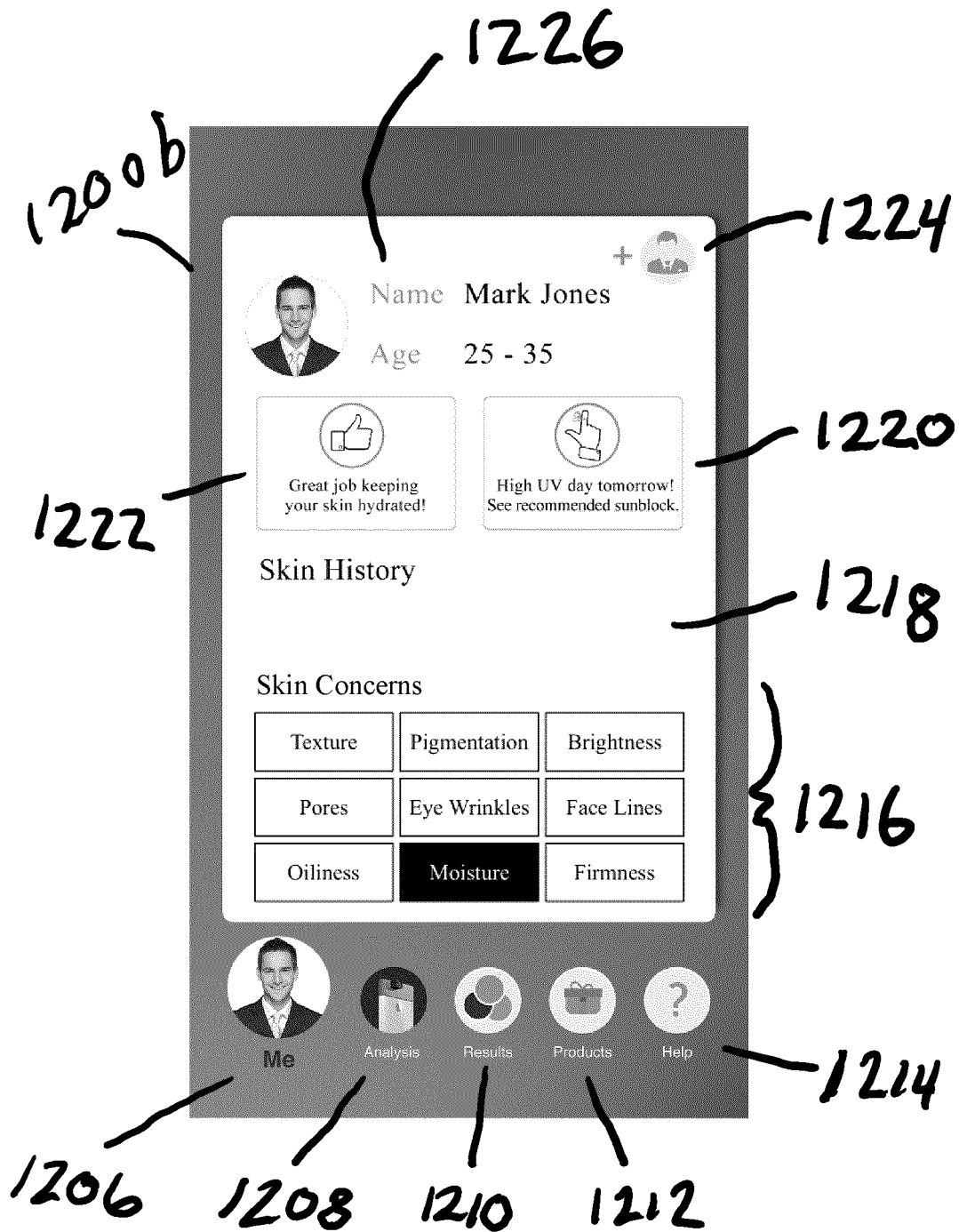
Figure 12C:
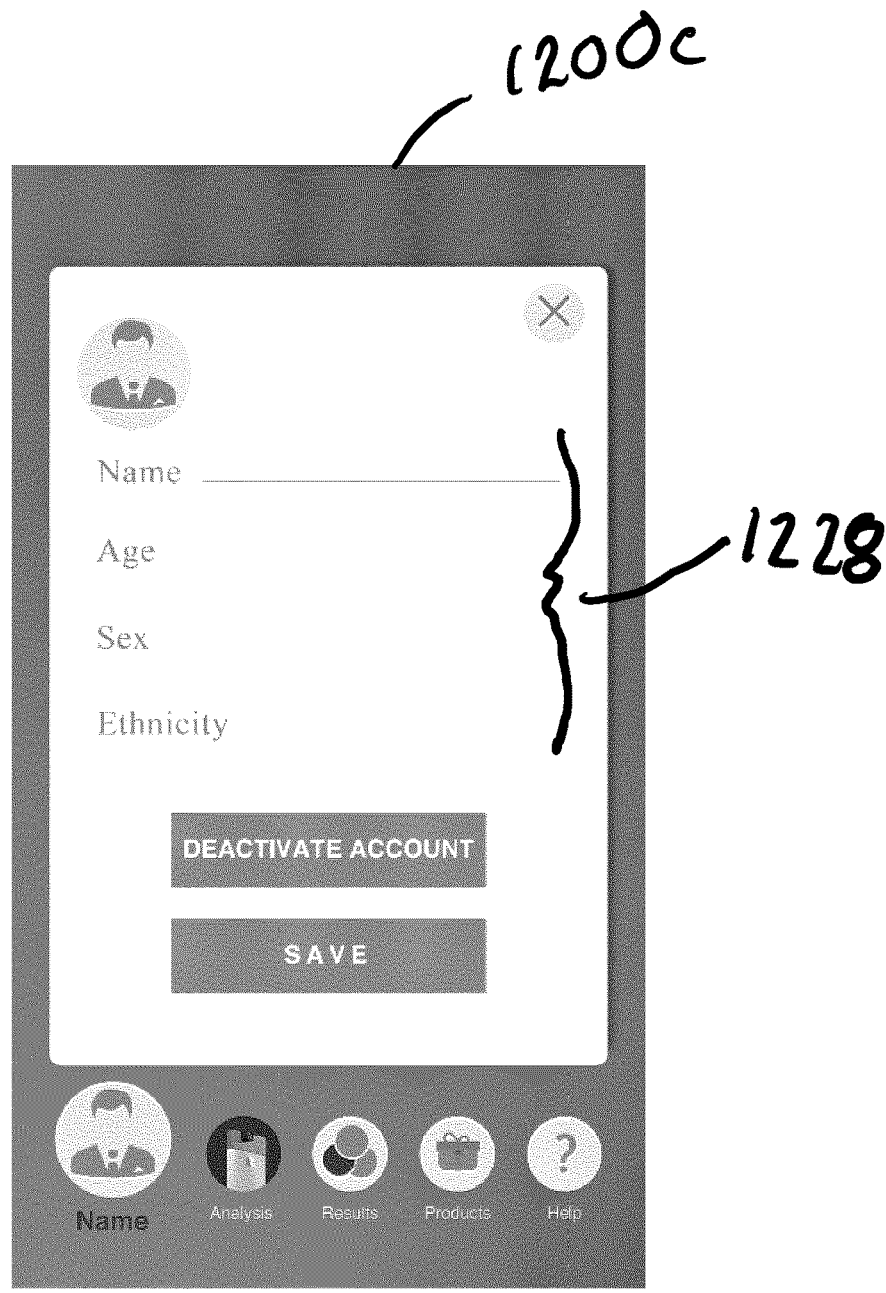
Figure 12D:
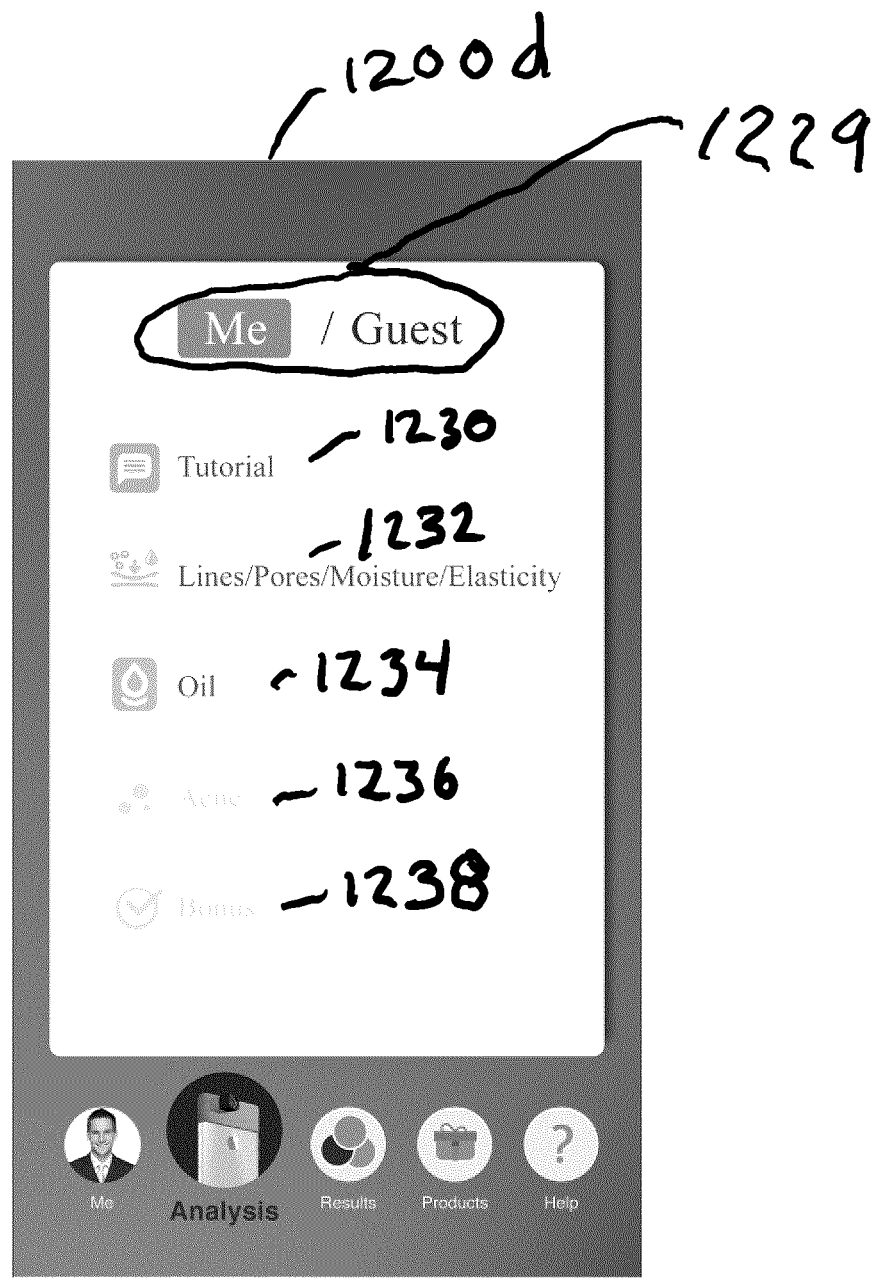
Figure 12E:
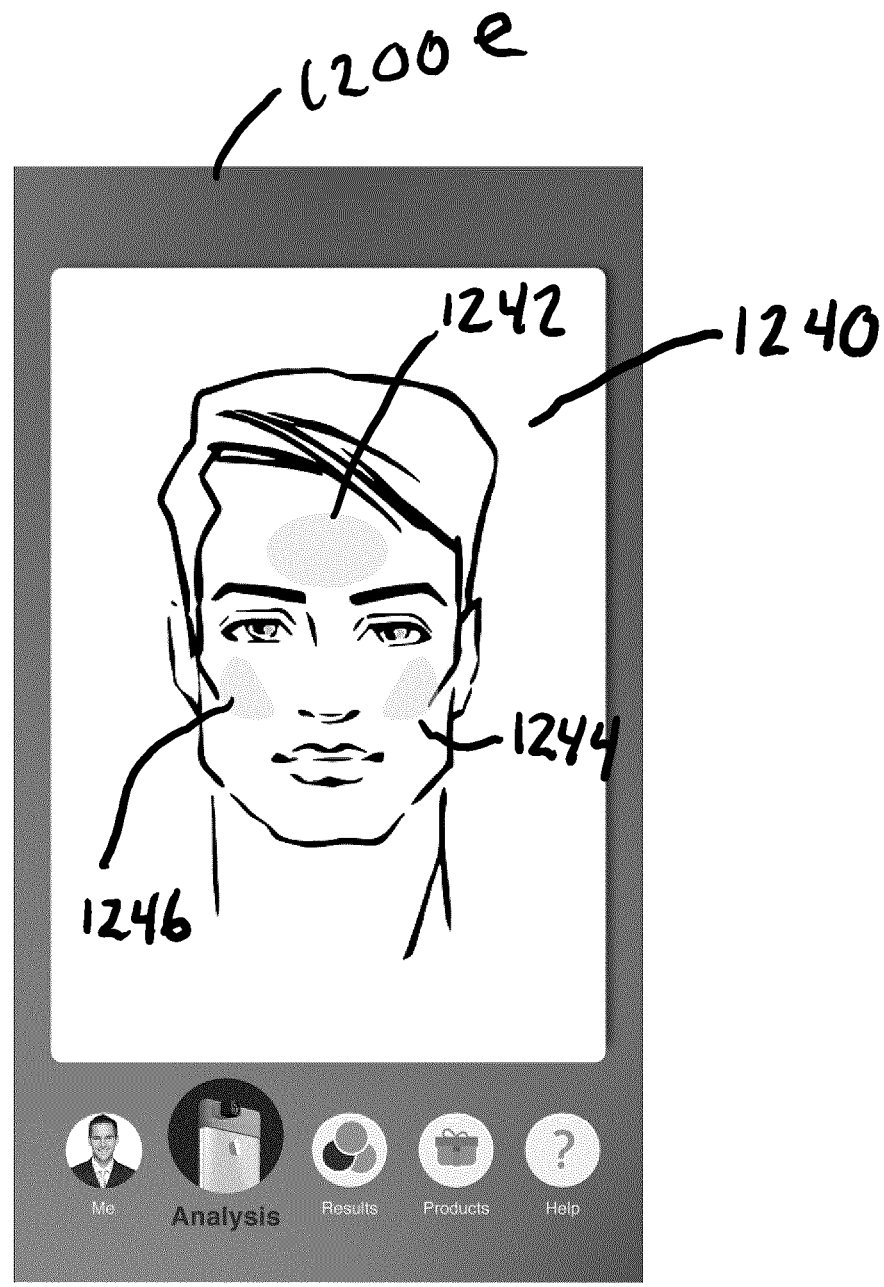
Figure 12F:
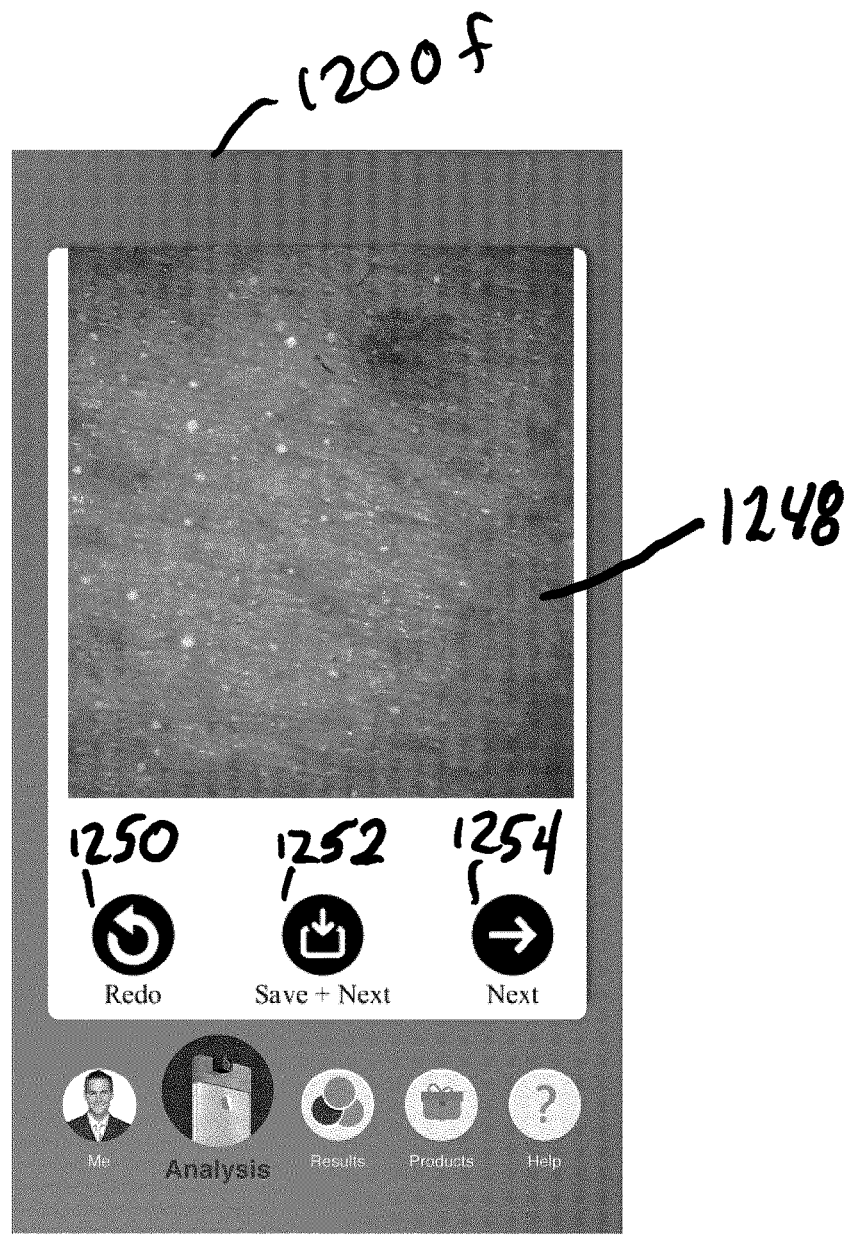
Figure 15:
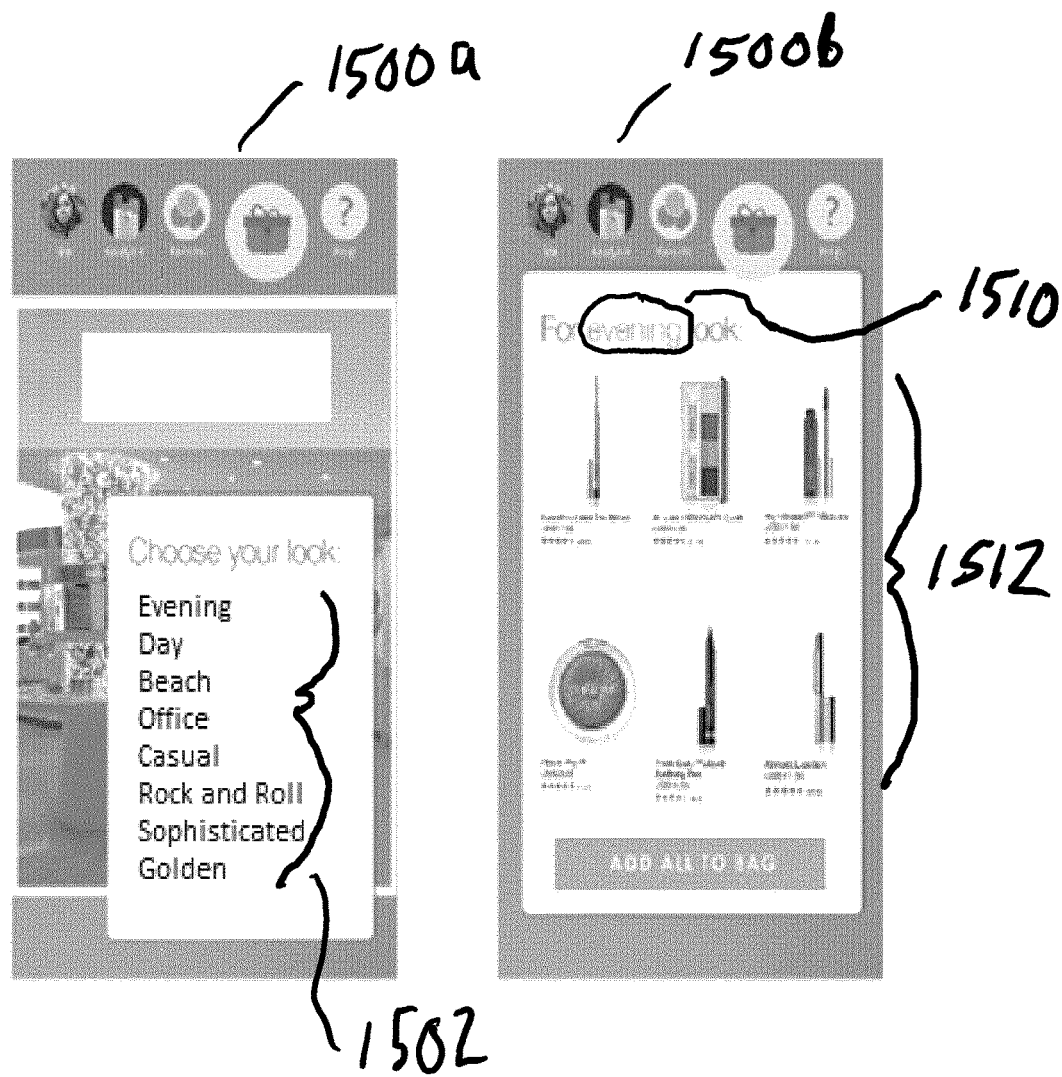
FIG. 15 illustrates screenshots of an app for an electronic device according to an aspect of the present invention.

(A) Example: grayMatrix[x][y]=meanVal−grayMatrix[x][y]. So the new Grayscale Matrix will be the old matrix subtracted from the mean value.
(vi) For each pixel of the new grayscale matrix:
(A) Take a 7×7 window around the pixel, or smaller if the pixel is close to the edge (a window of pixels).
(B) In this 49 pixel square, count the ones which have a pixel color value bigger than 23 and smaller than 90 (such being a specified range).
(C) If more than 20 of the 49 pixels, for example (20 out of 49 being a first quantity of pixels) at step B) qualified, then make the center pixel white (ie the pixel on which we started the process at step vi). Otherwise the relevant pixel will be set to black.
(vii) At this point we have a pixel matrix that has only black or white values (after the iterations at step vi).
(viii) A score will be the total number of white pixels from the image, which may be achieved by counting at the end or incrementing a white pixel counter as pixel colors are set to white.
(ix) Exemplary results may be as shown in image 1620.
(c) Oil processings
(i) System 1 looks for corneform and proprioni bacteria florescence. These bacteria thrive on sebum (oil). The oilier the human face, the more bacteria can be seen.
(ii) Thus, the user's skin is exposed to UVB light (370 nm wavelength), such as via second light source, and an image is obtained.
(iii) The image is converted to L*ab color space.
(iv) Pixels are searched for any pixels in the specific color range of the florescence and such pixels are counted.
(v) The total count of pixels in such color ranges produces a measurement of the surface area of the bacteria.
(vi) Exemplary results may be as shown in image 1660.
(d) Elasticity processings
(i) Two methods may be used, generally based on capabilities of camera 12 and electronic device 10:
(A) Method 1, for example for electronic devices 10 with more limited functioning, for example that cannot record in slow motion, high frame rate HD video:
(I) Using the user's age and moisture perform a correlation to determine an estimate for elasticity using one of several equations, though in general the higher the moisture, the greater the elasticity; the higher the age, the lower the elasticity.
(B) Method 2, for electronic devices 10 having suitable features:
(I) The user's skin is vibrated (using vibration motor) while a recording video is taken by a camera, for example filming at 240 frames per second. The length of time of the vibration and the intensity of the vibration (for example the speed/RPM of the motor) may be configured and may change for various electronic devices 10.
(II) App 18 then determines the amount of movement of the skin. More specifically, app 18 measures the amount of time it takes for the skin to 'rebound' or return to its original position, after the vibration has stopped. The more elastic the skin, the faster it will return to its original position. This may be based on, for example, tracking the motion of various pixels, groups of pixels, or areas of skin or tracking the number of pixels that enter and/or exit the field of view. App 18 may activate one or more starts and stops ("bursts") of vibration motor may be taken in one sampling, for example, and then process a set of such recordings of amounts of time. One or more locations can be measured and averaged to obtain a score.
(III) One or more measurements may be obtained or calculated from the determination.
a. Absolute score: An absolute score may be obtained from a particular combination of elasticity test parameters (motor RPM, time on, size of field of view, electronic device 10 model/version, skin analysis device 20 model/version, which may not be required for the elasticity test for example). For example the absolute score may be between zero and one million. Absolute scores may be normalized to a 'normal' set of elasticity test parameters, to allow for better relative scoring.
b. Relative score: a relative score may then be obtained, comparing a user to other users, for example having similar demographics (as described herein).
(e) Sunscreen processings
(i) We use the UVB light, for example from second light source, to capture a reference image, before sunscreen is applied (blocking UVB light may be required for such functioning to work, unless second light source also has UVA light).
(ii) Then an image of the user's skin is taken after sunscreen is applied. This may be whenever a user decides to take another image, or app 18 may be configured with a reminder schedule.
(iii) The image displays a green hue shift (as UVB light cannot penetrate and reflects back with a yellow hue, making the image appear green). This green shift fades back to blue gradually, as the sunscreen wears off and the second light. As the image becomes bluer then more sunscreen needs to be applied. Hence a green hue score may be calculated and a blue hue may be calculated, for example by considering the pixels in the images. Thresholds may be set to indicate to a user, via app 18, to re-apply sunscreen. These may include absolute thresholds (such as a threshold blue score) and relative thresholds (such as a reduction threshold indicating a reduction in blue score from an image before and after applying sunscreen).
(f) Color matching processings:
(i) Color matching broadly consists of two steps—color determination (determining a color for a user have a particular user face color—"determined color") and color matching (taking the determined color and matching it to an available shade of skin care product, possibly using a skin care product color guide, that may have color values for each product shade).
(A) Color determination may follow these steps:
(I) Generally, obtain one or more images of one or more areas of a user's face. For example, three images may be taken, using the same procedure as for skin analysis (as described in method 1000 and FIG. 12*e*), except the images are of the neck, cheek, and forehead. These three images may be averaged, as described, to produce one color value.
(II) For each of the 3 images:
  a. Take the image;
  b. Normalize the colors, if normalizing is available (as described herein, for example using color calibrator 80), for example using RGB values;
  c. Perform a color correction transform to correct for any difference. For example if color quadrant 84 is black (0/0/0) and is in an image as 1/2/2/then each color's RGB values in the image need to be adjusted down by 1/2/2;
(III) Apply a Gaussian filter to blur the image slightly;
(IV) Convert each pixel from RGB to L*ab color space;
(V) Calculate the average L value for the entire image;
(VI) For each pixel compare its L value to the average L value for the image;
  a. if the pixel's L value is in the top 25% darkest (ie within a dark threshold) or top 25% lightest (ie within a light threshold), then eliminate this pixel from consideration (eliminating the effects of skin color anomalies such as hair, blemishes, freckles, etc) (generally referred to as removing outlier pixels);
(VII) Calculate the average L, average A and average B values for the remaining pixels (an average color);
(VIII) Repeat the above for 2nd and 3rd images
(B) Obtain the average of the 3 L*ab values to get one L*ab value, and convert this to RGB (the determined color).
(C) Of course it is to be understood that different numbers of images, from different locations and different numbers of locations may be possible. Further, threshold values may be changed to suit.
(D) Compare against foundation color images:
  (I) Optionally perform hue filtering, comprising:
    a. Calculate the hue angle of the image from the determined color ("image hue angle");
    b. Specify skin care products to choose between for a specific product type ("total color options", for example for "foundation"—"foundation total color options").
      i. This may be done by app 18, a user, or a combination thereof.
      ii. Options for total color options include:
      a) All color options known to app 18;
      b) All color options known to app 18 that are owned by one or more vendors 300;
      c) All color options in a particular palette or collection, for example of one vendor 300;
      d) Colors in one or more skin care product color guides (which may be from one or more vendors 300).
      iii. Note that the hue angles of each skin care product image which may be pre-loaded into app 18, downloaded from SAS 200 or vendor 300, or even entered into app 18 using camera and skin analysis techniques described herein.
    c. Compare image hue angle to the hue angle of each of the total color options.
    d. Identify the top 5 (or any number) based on hue angle comparisons ("candidate hue matches").
  (II) Calculate the color difference between the user's skin and each of the candidate hue matches using a color difference formula such as CIE DeltaE 2000.
  (III) The lowest score from the color difference formula is the best matching color for ambient lighting that matches a sunny day (approximately D50, and optionally transformed to increase accuracy). Recall that skin images may be normalized to this light.
  (IV) A user may be asked what lighting they intend to use the skin care product in (such as evening, day, beach, office, as in 1502 of screenshot 1500*a*, which may allow app 18 to assume characteristics of the applicable lighting), and/or what atmosphere or look they desire (such as casual, rock and roll, sophisticated, as in 1502 of screenshot 1500*a*, which may allow app 18 to assume factors, such as boldness, when determining a color match or adjusting matches). That may alter the recommended color, for example by applying method 1300*a*. Such user interactions may be as shown in FIG. 15 and screenshots 1500*a* and 1500*b*.

Steps 1010 and 1012 may largely be performed on or by electronic device 10 and/or skin analysis device 20. However, other aspects of system 1 may be involved, such as SAS 200, for example if greater processing power or storage space is required.

At this point method 1000 may have substantially completed processing of a skin analysis measurement sample for one or more skin analysis measurements. This may result in having a skin analysis sample. Such a sample may have one or more raw images, one or more processed images, a user identifier, a date and time stamp, and other related information. Images may be uploaded to SAS 200 in real-time, being sent from electronic device 10. The user's sex, age, GPS coordinates, and other potentially non-personally identifying information can be stored (or personally identifying as required/desired, pursuant to applicable privacy requirements). Processing, as described herein, can occur on the device and/or on SAS 200 and/or on product owner 300 depending, for example on how intensive the processing is, what is to happen after the processing, and what entity/entities are to have a copy of the data when all is complete.

In one example of a skin characteristic sample the sample (or skin characteristic sample data structure) may include one or more of the following:
  (a) Six image files (unprocessed, color, two each from three locations or as configured), exemplary images including 1610, 1630 and 1650;
  (b) Optionally one or more processed version of the unprocessed images, exemplary images including 1620, 1640 and 1660;
  (c) Absolute scores for all skin analyses;
  (d) RGB value for skin color;
  (e) One or more moisture readings (absolute and/or normalized);
  (f) Personal information (name, age, ethnicity or race, GPS coordinates if allowed, gender, and the like); and
  (g) Past samples or trend information.

Figure 14A:
FIGS. 14a-d illustrate screenshots of an app for an electronic device according to an aspect of the present invention.
Figure 14B:
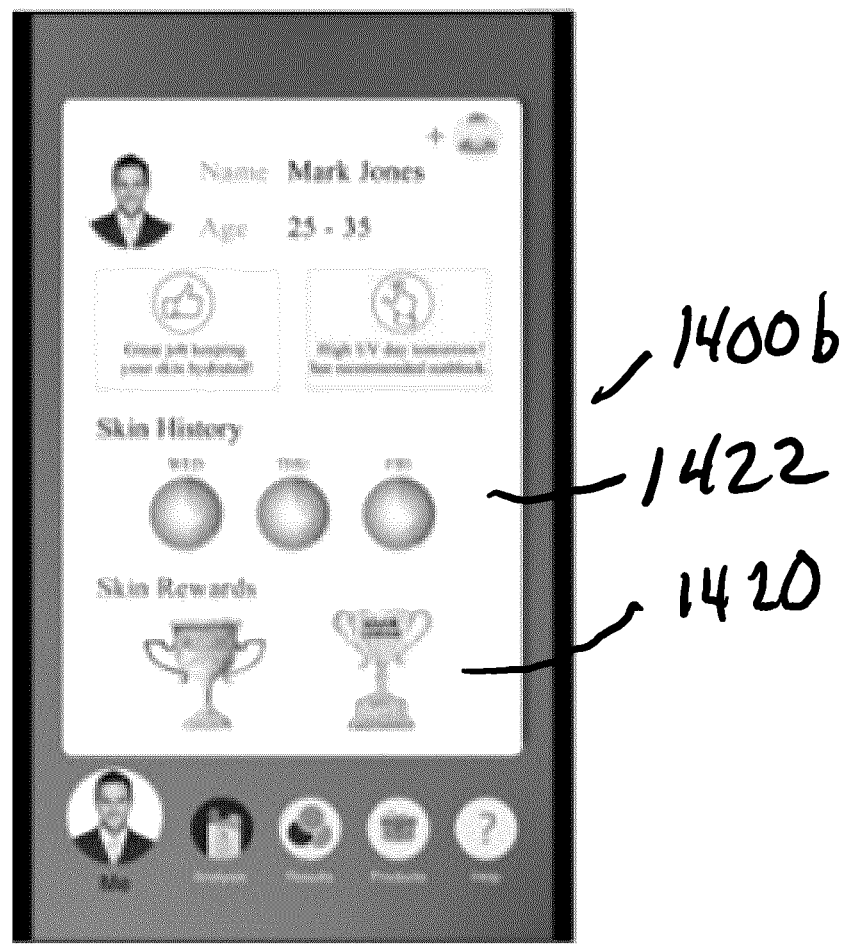
Figure 14C:
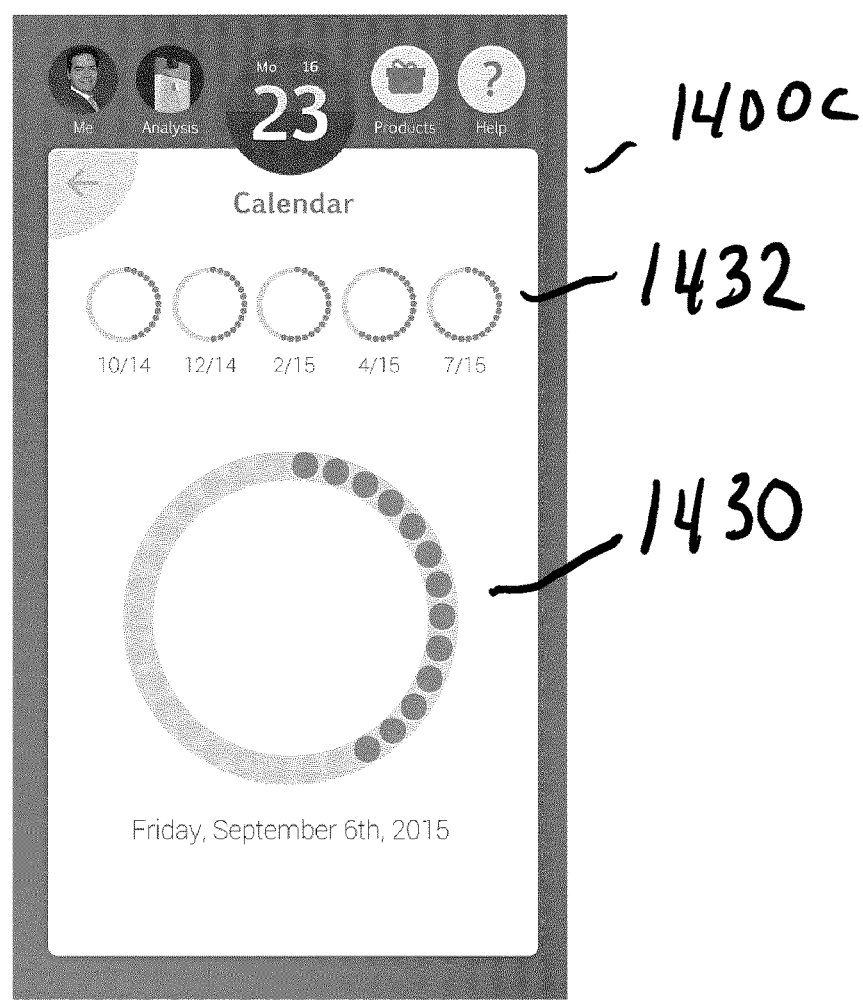
Figure 14D:
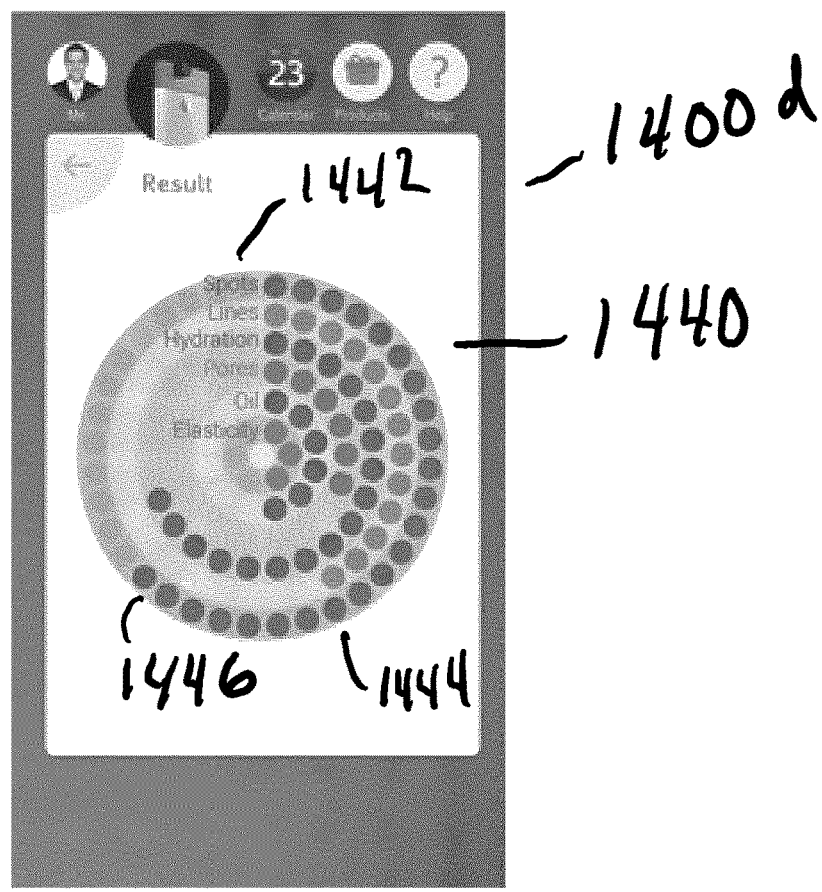

Method 1000 then continues to 1014 to begin the calculations and processing required for analysis to be presented. The steps performed at 1014 will depend greatly on the analysis, however the collected sample may, at 1014, be compared to one or more collections or subsets of samples stored at SAS 200 that may relate to the current user (for comparison to themselves over time, such as in FIG. 14c) or comparing the current user to all users in SAS 200 (or for product owner 300) in the user's demographic (such as in FIG. 12g, UI element 1260).

Method 1000 then continues to 1016 where results may be shown to the user, for example on one or more screenshots of app 18 (for example as shown in FIGS. 12g and 14a-d.

Method 1000 then continues to 1018 where a recommendation algorithm is performed. Of course 1018 may occur before 1014/1016 or simultaneous therewith. Recommendation algorithms may exist for each skin characteristic, and even for various combinations of skin characteristics. Recommendation algorithms may be substantially the generic recommendation algorithms described herein, which may be performed by app 18 and/or SAS 200. In such cases app 18 and/or SAS 200 have the required data and can simply apply the recommendation algorithm. Alternatively, and for example where a product owner 300 has its own recommendation algorithm, the recommendation algorithms can be performed by product owner 300. In such cases app 18 and/or SAS 200 may provide data required for the recommendation algorithm ("recommendation required data") to product owner 300, and product owner 300 may communicate the recommended products (all the data required or a skin product identifier identifying a product whose information is stored in app 18) back to app 18.

Figure 12G:
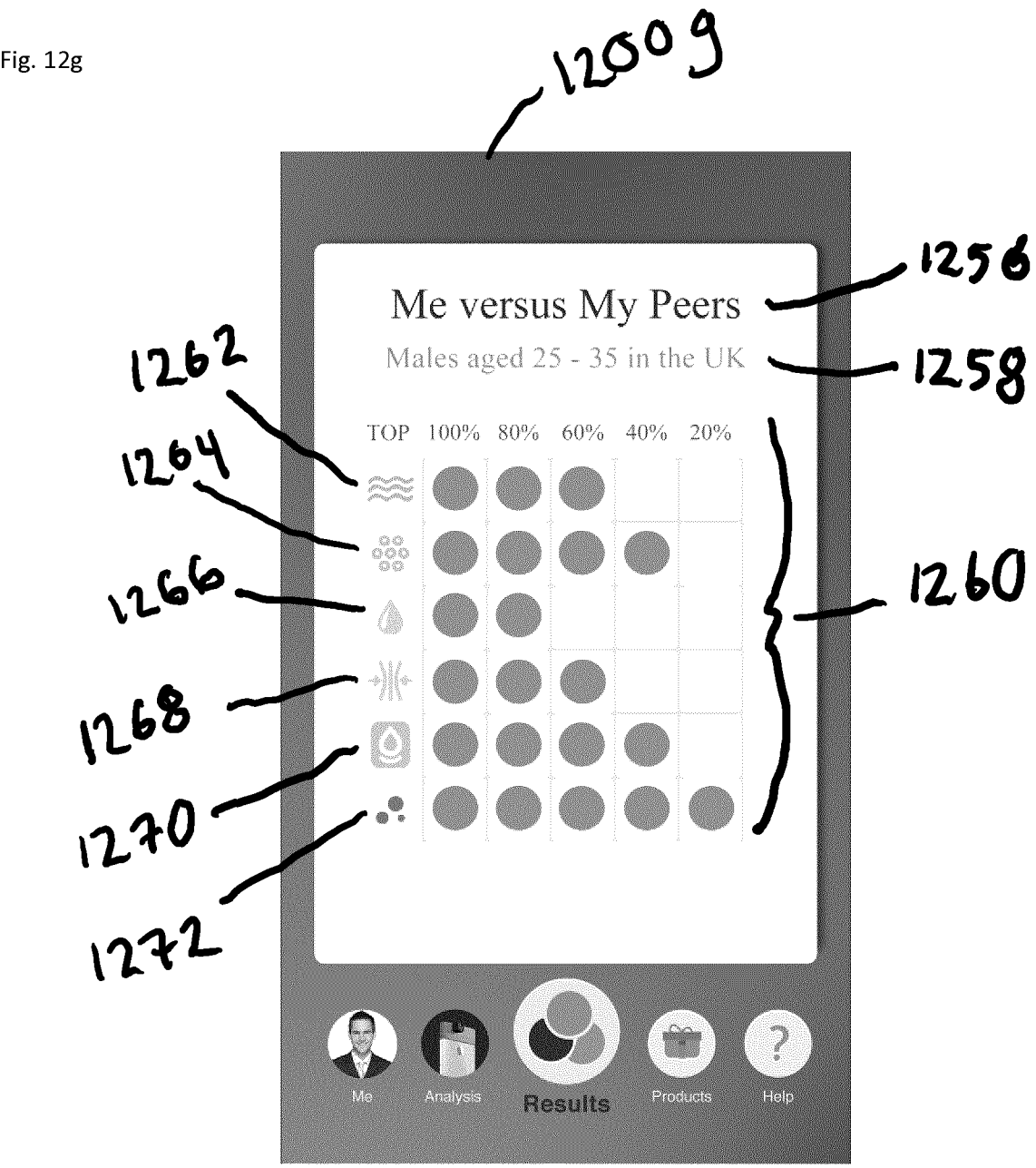
Figure 12H:
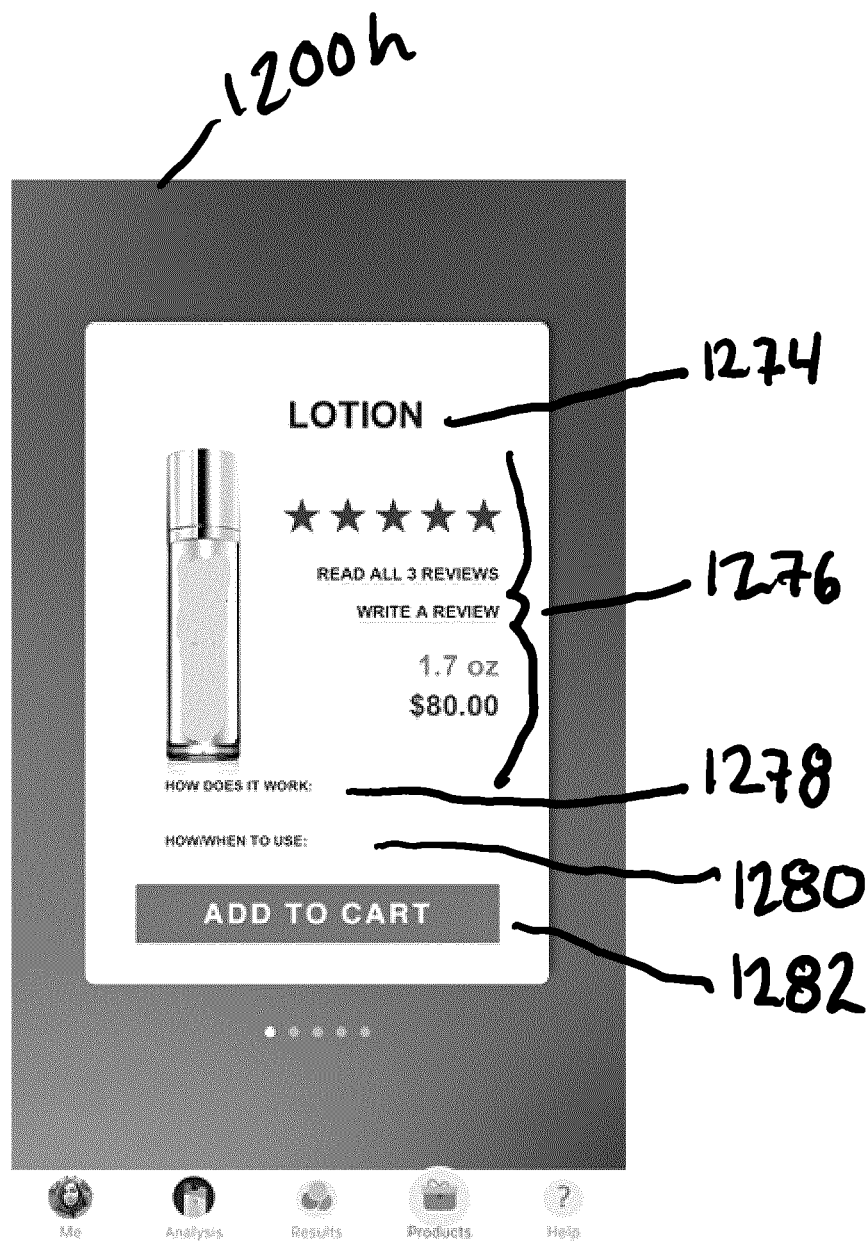
Figure 12I:
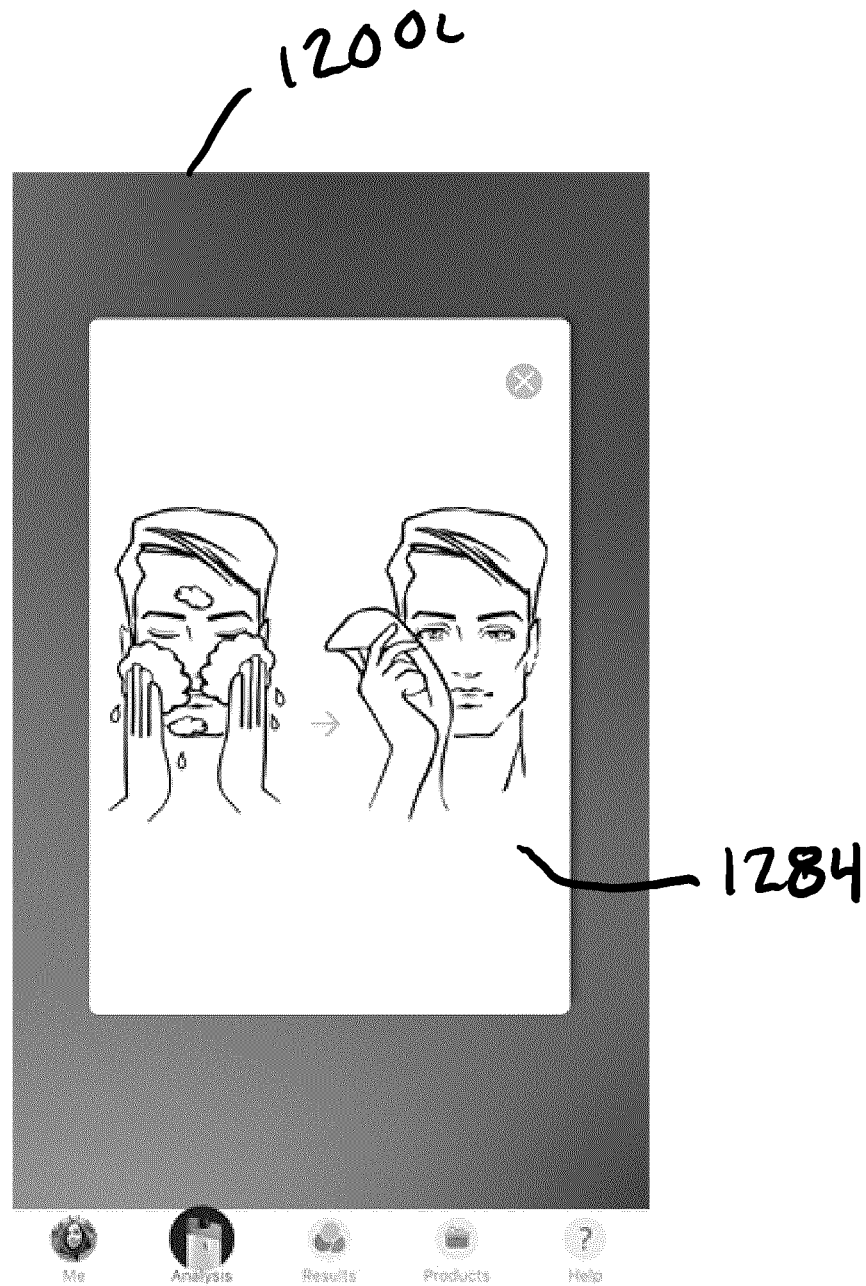
Figure 12J:
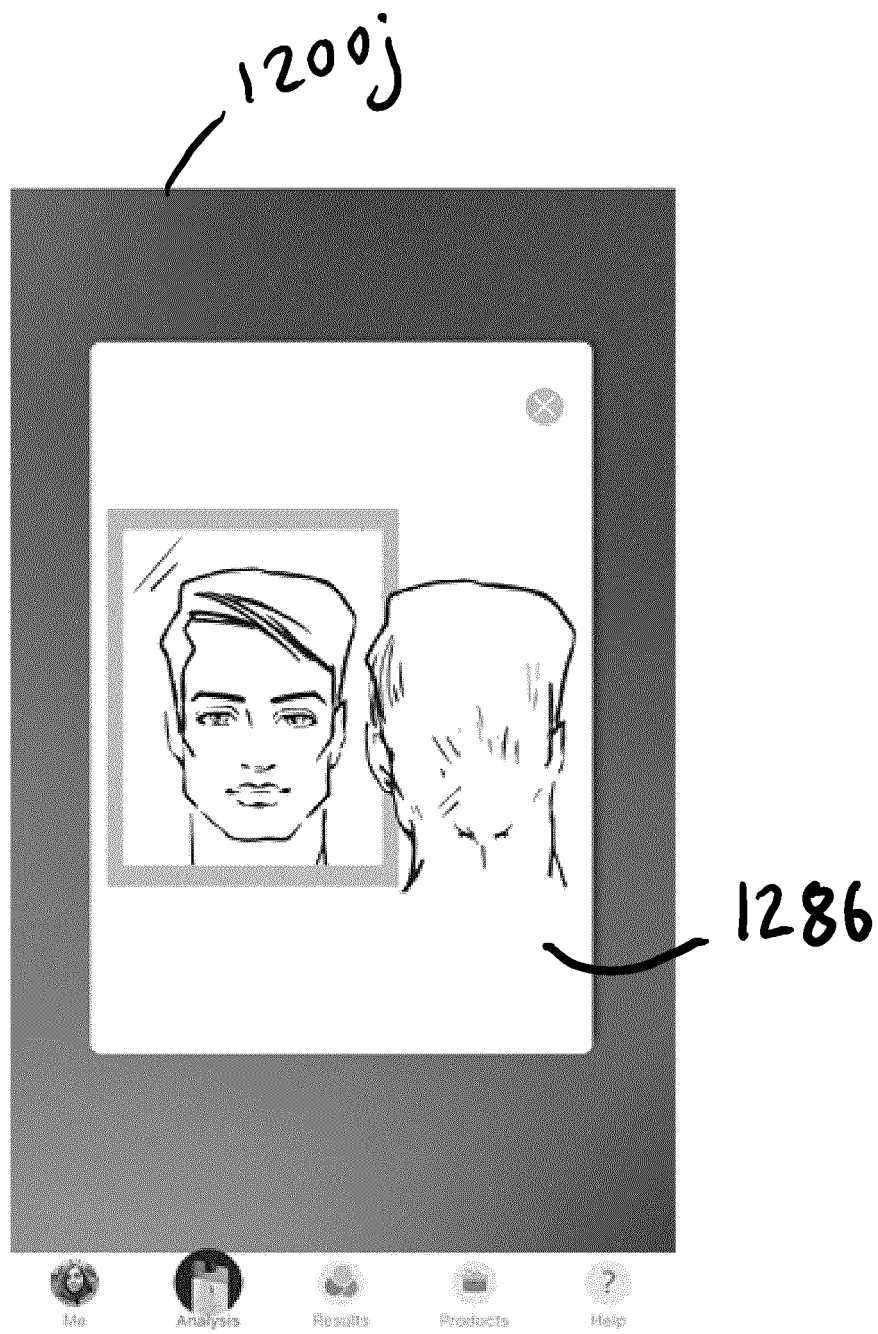
Figure 12K:
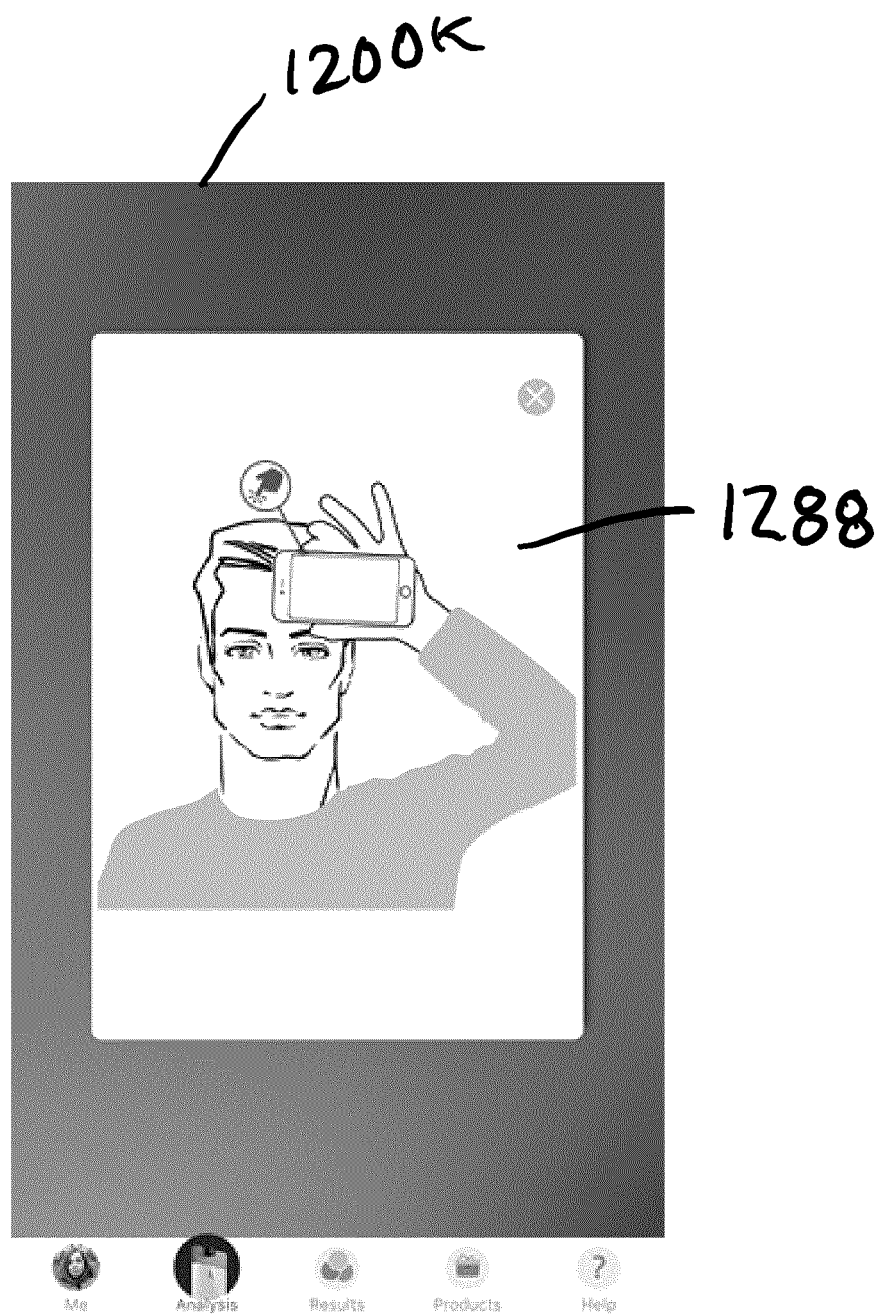
Figure 12L:
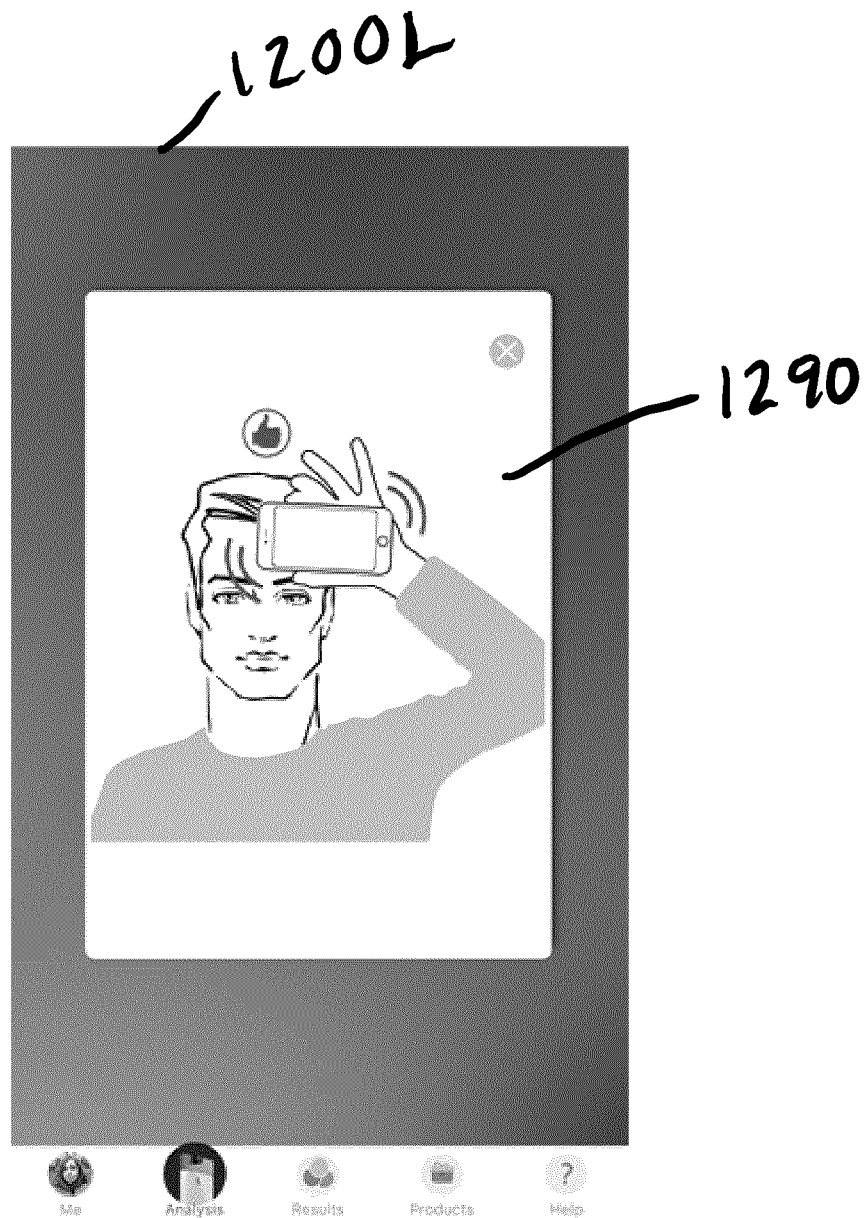
Figure 12M:
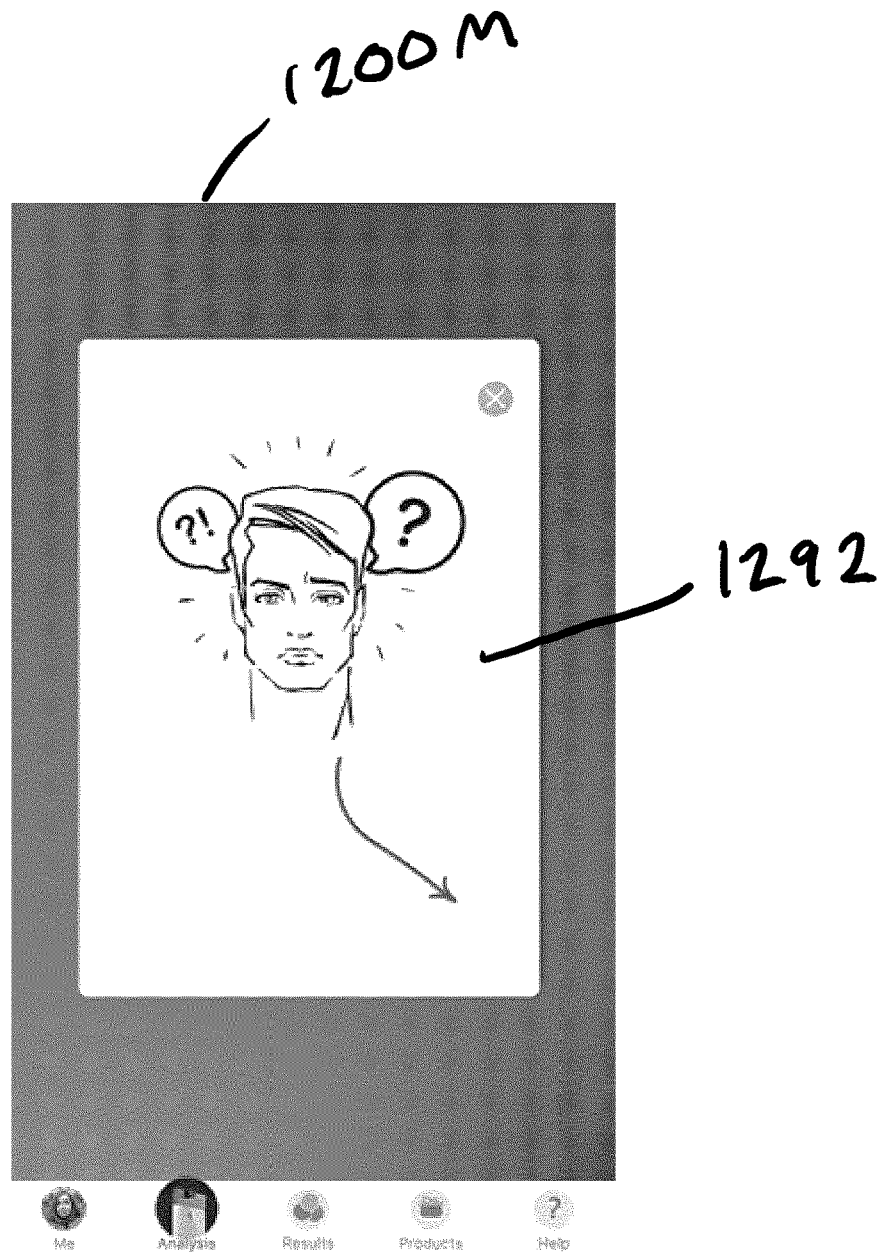

Method 1000 then continues to 1020 where one or more recommended products are displayed for a user to review and consider purchasing, for example as shown in FIG. 12h.

Steps 1018 and 1020 may be somewhat iterative, in that they may further involve prompting a user for additional information to better perform a recommendation algorithm. For example, a user may be doing a moisture analysis and they have dry skin. At 1018 a moisturizer may be recommended. However, after showing such recommended product, at 1020, or before, method 1000 may ask a user if they plan on using the product during the day and/or outside. If so the recommendation algorithm may change the moisturizer to a moisturizer with UV protection, particularly if skin care updates or external sources indicate high UV for where the user is located (as may be determined by a GPS location of electronic device 10).

FIG. 11 is a method 1100 for performing skin analysis measurements according to an aspect of the present invention. Method 1100 essentially addresses the methods for performing the recordation, or obtaining, the skin analysis measurements (with getting them into app 18, processing them, communicating them beyond app 18 being separate herefrom).

Method 1100 begins at 1102, having arrived from 1008, for example. At 1102 a query is made whether skin analysis device 20 (and/or electronic device 10) is in place. This may mean that skin analysis device 20 is being held on a user's face or body. In cases where one or more skin characteristics measurement devices and/or skin characteristic measurement assisters could be damaging (an adverse effect device—that may assist a skin characteristic measurement device take a skin characteristic sample of a user but may be dangerous to the user if used in an improper way), such a step may be desirable. For example, in one embodiment second light source 74 may be UV and may be damaging to eyes, or other light sources that may be damaging (lasers, infrared, and the like). At 1102 moisture sensor 36 (in such an example a safe use indicator device) may be queried and if a reading from moisture sensor 36 indicates that the user has skin analysis device 20 in place (in such case such reading being a safe use indicator signal) then the method may proceed, and in particular before UV lights are turned on in a safe use. Of course it may be desirable to assure skin analysis device 20 is in place before performing method 1100, for example to help preventing improper images from being taken. Alternatively these queries may be performed just before the particularly problematic/dangerous skin characteristic measurement device is activated.

If skin analysis device 20 is not in place then at 1104 method 1100 may wait.

Continuing, method 1100 arrives at 1106, where a loop (of 1106-1120 or 1122) may begin for each skin characteristic measurement that is to occur. Broadly speaking there may be imaging and moisture sensor reading. However, among imaging there may be slightly different performance of 1106-1120, for example for lines/wrinkles, oil, elasticity, etc, based on what devices and assisters may be used.

Returning to 1108 a query is made whether, for the given skin characteristic measurement, if the required skin characteristic measurement device(s) are ready. By way of example, camera 12 or moisture sensor 36 may need to be turned on, or warmed up, in particular if they have not been used recently (as known by app 18). If they are not ready then method 1100 waits at 1110 and prepares them.

At 1112 a query is made whether, for the given skin characteristic measurement, if the required skin characteristic measurement assister(s) are ready. This is much the same as for the skin characteristic measurement devices in 1108 and 1110. By way of example, first light source 72 may preferably be warm before being used (making its light spectrum more consistent).

At 1116, having been assured that the required components were ready, each skin characteristic measurement assister may be activated (one or more for a given skin characteristic measurement). For passive skin characteristic measurement assisters this may not be required (ie lens 34 may already be in place). For active skin characteristic measurement assisters this may be:
  (a) app 18 communicating with processor 132 (for example via Bluetooth) to:
    (i) turn on first light source (non polarized) in preparation for an image being taken, for line processing;
    (ii) turn on second light source in preparation for an image being taken for oiliness;
  (b) app 18 communicating with the assister, for example via API:
    (i) turn on vibration motor in preparation for a images (such as video) being taken for elasticity.

At 1118, each skin characteristic measurement device may be activated (one or more for a given skin characteristic measurement), possibly after a delay to ensure assisters are sufficiently prepared (for example 1 second after a particular light source is activated). This may involve:
  (a) App 18 using API to prepare camera 12 and then accept an input from a user (such as volume up button being pushed) or a timer to automatically take an image;
  (b) App 18 using API to turn on 'live preview' (for lines/pores/moisture/oil for example);
  (c) App 18 communicating with processor 132 (for example via Bluetooth) to obtain begin communication with moisture sensor 36.

At 1120 skin characteristic measurement device and skin characteristic measurement assister that was activated may be deactivated (for example turning off first light source 72).

At 1122 method 1100 may confirm that proper functioning occurred. This may be via logic on app 18 and/or via inputs from a user (for example indicating acceptable image quality). This may be performed using screenshot 1200f, for example.

Method 1100 may then return to 1010, as described herein.

It is to be understood that although 1106-1122 are described "for each skin characteristic measurement" several may be combined in quick succession. For example one or more may be initiated at the same time, such that the above control (ie turning on and off various light sources in advance and in between taking various images) may be abstracted from a user. A user, or logic in app 18, may select one or more skin characteristic measurements and once a user places skin analysis device at a first skin location the required steps may be taken without further user input.

In one exemplary embodiment, lines, oiliness and moisture are the skin characteristic measurements. Assuming method 1100 had reached 1116 (ie camera 12, lens 34, first light source 72 and moisture sensor 36 were prepared), the following might occur:

(a) First light source is turned on;
(b) An image is taken;
(c) First light source is turned off;
(d) Second light source is turned on;
(e) An image is taken;
(f) Second light source is turned off;
(g) Moisture sensor is activated;
(h) Processor obtains a moisture sensor reading;
(i) Moisture sensor is turned off.
(j) App 18 ensures that the two images and moisture sensor reading appear acceptable (for example in combination with a user indicating so) and method 1100 ends.

FIGS. 12a-m illustrate screenshots of app 18 for electronic device 10 according to an aspect of the present invention.

Screenshots 1200a-m show various screens of app 18 that may be shown to a user to allow a user to access the functionality described herein. Each of such screens may include one or more user interface (UI) elements (buttons, text, widgets, icons, pictures, drop-down lists, tabs, infographics, and the like). It is to be understood that screenshots 1200a-m and the UI elements shown are exemplary only—many designs, layouts, orderings and styles of screens, UI elements, and features may be conceived to implement the functionality and aspects of the invention as described herein.

Beginning at screenshot 1200a a user may be presented with buttons 1202 or 1204 to select what they would like to do first. Of course all buttons herein may be accessed using user inputs (such as pushing the button on the screen or using a pointing device). If a user selects button 1202 they may begin a skin analysis, as described herein. If a user selects button 1204 they may begin finding a product, as described herein.

At screenshot 1200b a user may be presented with the following UI elements:
(a) Tab selectors 1206-1214: A user may toggle between areas of app 18, such as:
  (i) "User Info" 1206: where a user may specify and view stored information about them, such as shown in screenshot 1200c and as shown in user info area 1226.
  (ii) Analysis 1208: where a user may be shown several screenshots (such as 1200d-f) to initiate and take steps to perform skin care analysis.
  (iii) Results 1210: where a user may be shown several screenshots (such as 1200g and 1400a-d to view results of the analysis.
  (iv) Products 1212: where a user may be shown several screenshots (such as 1200h) to view recommended products, and optionally initiate purchasing thereof.
  (v) Help 1214: where a user may be shown several screenshots (such as 1200i-m) to provide tutorial information about how to perform the steps for analysis or otherwise use system 1 and the components thereof as described herein.
(b) UI element 1216 may be a collection of UI elements that show various aspects of a user's skin (skin characteristics), allowing a user to specify aspects they are concerned about. These selections, when a user then toggles to "Analysis" may pre-select or initiate the steps or functionality required to analyze the selected skin characteristics. Others may be added over time and some may not be shown but may be included, such as sunscreen, as described herein. As an alternative to UI element 1216, UI element 1420 may be displayed on screenshot 1200b; such UI element 1420 may show rewards or awards that a user has won, for example based on historical skin analysis results. Such may provide free or discounted skin care products, for example, or other recognition, for example versus peers or on a skin care "leader board".
(c) UI element 1218 may show a user's skin history. For example a chart or summary of moisture levels over a period of time, such as a summary of what is shown at 1422 in screenshot 1400b of FIG. 14b or in 1432/1430 of screenshot 1400c in FIG. 14c.
(d) UI element 1220 may show skin care updates and may include a link to a recommended product (such as "tomorrow will be a high UV day, so wear sunblock", and pushing UI element 1220 may take the user to a screenshot, such as 1200h that may have sunscreen pre-selected based on the user and their skin characteristics.
(e) UI element 1222 may show current feedback to a user, for example highlighting trends about their skin characteristic samples or comparisons to others.
(f) UI element 1224 may show an icon to add a user profile (either a first user profile for app 18, or an additional user profile).
(g) UI element 1226 and 1228 (FIG. 12c), may show user information and allow entry thereof. Such user information may allow results to be shown based on demographics (ie age, sex, ethnicity) and may make results more accurate and provide a quality control check (ie if ethnicity is "person of color" and a skin analysis measurement indicated very white skin then a confirmation may be sought).

At screenshot 1200d a user may be presented with the following UI elements:
(a) UI element 1229: may allow app 18 to toggle between obtaining a sample for the logged in user and a guest, such that a particular electronic device 10 (having skin care analysis device 20) can be shared between friends.
(b) UI element 1230: may allow a user to jump to a tutorial for how to use app 18 and skin care analysis device 20.
(c) UI elements 1232-1236: may allow a user to initiate one or more analyses of one or more skin characteristics, such as lines/pores/moisture/elasticity 1232, oil 1234, and acne 1236. One or more of such UI elements may be disabled (not selectable). This may be, for example, if the required skin analysis measurement devices or skin analysis device assisters are not available on either skin analysis device 20 or electronic device 10. Other such UI elements may be added, such as for sunscreen, and other analyses that may later be added.

At screenshot 1200e a user may be presented with a picture of a user 1240 and various sample locations 1242, 1244, 1246 that a user is to apply skin analysis device 20 to, in order to perform the intended analyses.

At screenshot 1200f a user may be presented with an image that was taken 1248 (noting such may be post-processing in FIG. 12f), with buttons to redo 1250, save and take the next image 1252 (ie save a copy of the image on electronic device 10) and go to next 1254 (ie the image will be used but not saved in a photo album on electronic device 10).

At screenshot 1200g a user may be presented with results of their skin care analyses. Such results may be described based on the type of result 1256 and aspects of the type of result 1258. In the present example the type is versus peers and the aspects are same sex, same age range and same country. Types may also be against myself, with an aspect being historical. Results may be shown in a results summary infographic 1260, which may include percentiles for results of lines 1262, pores 1264, moisture 1266, elasticity 1268, oil 1270 and acne 1272.

In 1260 percentiles may be assigned for each result (noting being in the 100% percentile is more desirable in FIG. 12g, though any nomenclature may be used). These percentiles may be generally calculated, for the various skin characteristics, as such:

(a) Lines 1262: More lines and/or thicker lines is generally worse. The surface area and total number of lines in the image may be counted. Then a line/unit area may be computed. This "line score" may then be compare against users in the same demographic, with the lower scores being in the lower percentiles.

(b) Pores 1264: More and/or larger pores is generally worse. The total number of pores detected in the image may be counted. The surface area represented in the image may be determined. Then a pore/unit area may be computed. This "pore score" may then be compare against users in the same demographic, with the lower scores being in the lower percentiles.

(c) Moisture 1266: Generally, the more moist the skin, the better. The moisture score, generally a numeric value (possibly normalized as described herein) may be compared against users in the same demographic, with the higher scores being in the lower percentiles.

(d) Elasticity 1268: Generally, the more elastic the skin, the better. The elasticity score may be compared against users in the same demographic, with the higher scores being in the lower percentiles.

(e) Oil 1270: Generally, the less oily the skin, the better. The oil score may be compared against users in the same demographic, with the lower scores being in the lower percentiles.

(f) Acne 1272: Generally, the less acne on the skin, the better. The acne score may be compared against users in the same demographic, with the lower scores being in the lower percentiles.

(g) Sunscreen (see 1400a): Generally the better sunscreen coverage the better. That means the greener the image the better, as bluer indicates wearing off of the sunscreen. A blue score may be applied and results displayed to indicate whether a user has adequate sunscreen, in particular as compared to current weather/UV (as may be shown in 1402).

As noted, screenshot 1200 is an exemplary screenshot that may show results. Another exemplar screenshot, showing results without a comparison, may be seen at screenshot 1400d in FIG. 14d. In such screenshot 1400d UI element 1446 may show various skin characteristics (1442) and the results/scores thereof (1444).

At screenshot 1200h a user may be presented with the recommended product 1274, along with information about the recommend product 1276 (such as a rating, reviews and links thereto, volume information, and price). Notably, ratings and reviews from other users may be specific to users with similar skin types and/or skin tone—thus increasing the value of the ratings and reviews—for example by filtering ratings and reviewers. Information about the recommended product may further include how it works 1278 and instructions for use 1280. A user may select button 1282 to initiate the purchase of recommended product, for example by placing it in a cart (as known in the art) which may be a cart on app 18 and/or an app of vendor 400.

At screenshots 1200i-m a user may be presented with various images 1284, 1286, 1288, 1290 and 1292 that provide instructions. Of course these may be accompanied by text, if desired. In general, and as further described herein, a user will wash their face, ensure it appears 'normal' (ie no dirt or makeup abnormalities), position the skin analysis device appropriately and click a button on electronic device 10 (such as volume button) to initiate an image being taken by camera 12 (as in 1288), and wait for a response from app 18 to indicate they can move to another location or the image taking is complete (such as via an audible signal or a vibration).

FIGS. 13a-b are methods 1300a and an example thereof for color matching for different lighting according to an aspect of the present invention.

The goal of method 1300a may be to determine, based on light other than ambient light (as may be specified by a user—for example outdoor, very bright for television, darker than indoor, etc), and potentially a mood or persona the user wants (such as rock and roll in 1502—a "mood"), whether a color shade other than mindE may be preferable for the desired user, light conditions and persona. Method 1300a, as described, considers that images (and hence mindE) are based on ambient lighting at capture (optionally normalized to such lighting but referred to as "capture lighting") and then a user may want a recommended product/shade for outdoor or indoor lighting (each "alternative lighting" having "alternative lighting characteristics", such as in 1502). Of course different capture lightings and different alternative lightings can be used, and all of the configurable parameters can be adjusted to suit (parameters varying, for example on the nature of the differences between the capture lighting and the various alternative lightings). The goal is to alter mindE if a more suitable shade exists for the lighting/persona the user intends to use the skin care product in (such more suitable shade being a "contextual suggested product color").

Method 1300a begins at 1302 where the minimum dE (minimum color difference) and resulting color (mindE color) is found, as described herein (for example of the candidate hue matches or the total color options).

At 1304, the dE values are found for color shades that are +1 and +2 shades darker than mindE color (ie mindE1C and mindE2C, or one shade darker and two shades darker). The dE values between shades are then found at 1306.

At 1308 a query is made whether mindE1 minus mindE is less than or equal to 1 (where one may be configured but is the dE between shades in the selection of color options. Of course if there are many shades in the color option there is a higher likelihood that the next shade darker is close to mindE (meaning that the query at 1308 is more likely to be "yes").

At 1310, if the answer is yes then the recommended product for outdoor use (assuming such use was specified) would be mindE1.

At 1312 a query is made if mindE2 minus mindE1 is less than or equal to a configurable parameter (6 as an example for shades 1-6, using the color shades from screenshot 1350) and mindE2 minus mindE1 is less than or equal to a further configurable parameter (3 as an example for shades 7-10, using the color shades from screenshot 1350). If so then at 1316 mindE2C becomes the recommended product for indoor lighting (if a user asks for such a product recommendation, or it may be stored in app 18). If not then mindE1C becomes the recommended product for indoor lighting.

Returning to 1308, if the result of the query is "no" then method 1300 continues to 1318 where mindE becomes the recommended product for outdoor lighting.

Then at 1320 a query is made if mindE1 minus mindE is less than or equal to a configurable parameter (6 as an example for shades 1-6, using the color shades from screenshot 1350) and mindE1 minus mindE is less than or equal to a further configurable parameter (3 as an example for shades 7-10, using the color shades from screenshot 1350). If so then at 1322 mindEC becomes the recommended product for indoor lighting (if a user asks for such a product recommendation, or it may be stored in app 18). If not then mindE1C becomes the recommended product for indoor lighting.

Turning to FIG. 13*b*, screenshot 1350 may be an exemplary screenshot when "MyColor" tab 1356 is selected. Screenshot 1350 shows a measured skin color 1352 and one or more color options comprising the total color options for the particular color match, along with their color values. Tab 1358 may bring a user to a screenshot, which may be similar to screenshot 1200*h*, which has recommended products that may be color matched skin care products like foundation, blush, and the like.

At 1302*b* Medium Tan is determined to be mindE. Tan and Tan Deep are mindE1C and mindE2C respectively, at 1304*b*. At 1306*b* and 1308*b* the subtractions occur and result in values (0.925 and 3.197). Therefore Tan (mindE1C) becomes the outdoor recommended product or color match at 1318*b* and at 1322 Tan becomes the indoor recommended product or color match.

The embodiments of the systems and methods described herein may be implemented in hardware or software, or a combination of both. These embodiments may be implemented in computer programs executing on programmable computers or electronic devices, each such device including at least one processor, a data storage system (including volatile memory or non-volatile memory or other data storage elements or a combination thereof), and at least one communication interface. In certain embodiments, the computer may be a digital or any analogue computer.

Program code is applied to input data to perform the functions described herein and to generate output information. The output information is applied to one or more output devices, in known fashion. Such may be accomplished via applications that are operable on the electronic devices, for example.

Each program may be implemented in a high level procedural or object oriented programming or scripting language, or both, to communicate with and/or between computer systems. However, alternatively the programs may be implemented in assembly or machine language, if desired and/or as required by the particular processor or device. The language may be a compiled or interpreted language. Each such computer program may be stored on a storage media or a device (e.g., read-only memory (ROM), magnetic disk, optical disc), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the systems and methods of the described embodiments are capable of being distributed in a computer program product including a physical, nontransitory computer readable medium that bears computer usable instructions for one or more processors. The medium may be provided in various forms, including one or more diskettes, compact disks, tapes, chips, magnetic and electronic storage media, and the like. Non-transitory computer-readable media comprise all computer-readable media, with the exception being a transitory, propagating signal. The term non-transitory is not intended to exclude computer readable media such as a volatile memory or random access memory (RAM), where the data stored thereon is only temporarily stored. The computer useable instructions may also be in various forms, including compiled and non-compiled code.

It will be apparent to one of skill in the art that other configurations, hardware etc. may be used in any of the foregoing embodiments of the products, methods, and systems of this invention. It will be understood that the specification is illustrative of the present invention and that other embodiments within the spirit and scope of the invention will suggest themselves to those skilled in the art.

The aforementioned embodiments have been described by way of example only. The invention is not to be considered limiting by these examples and is defined by the claims that now follow.

What is claimed is:

1. A skin analysis device for attachment to an electronic device of a user, the electronic device having at least one skin characteristic measurement device, the skin analysis device comprising:
   an enclosure comprising an enclosure body, configured to be removably connected to the electronic device;
   one or more passive skin characteristic measurement assisters, connected to the enclosure and configured to assist one or more skin characteristic measurement devices in taking a skin characteristic sample of a skin characteristic of the user;
   a second skin characteristic measurement device, wherein the second skin characteristic measurement device comprises a moisture sensor, connected to the enclosure and configured to take a second skin characteristic sample of a skin characteristic of the user, the second skin characteristic sample comprising a moisture sensor reading; and a skin analysis device processor, in communication with the electronic device and the moisture sensor, the skin analysis device processor configured to:
obtain the moisture sensor reading, and a first autofocus distance when the moisture sensor reading is taken, from the moisture sensor, the user applying a first amount of pressure to the skin analysis device to touch the user when the obtaining occurs; and provide the moisture sensor reading to the electronic device;
calibrate the moisture sensor using a sensor autofocus distance calibration to adjust the moisture sensor reading based on an amount of pressure applied by the user when the moisture sensor reading is obtained;
determine a pressure-based moisture factoring value that can be applied to the moisture sensor reading, based on the first autofocus distance when the second skin characteristic sample is taken; and
apply the pressure-based moisture factoring value to the moisture sensor reading, to adjust for the first amount of pressure, resulting in an adjusted moisture level.

2. The skin analysis device of claim 1 wherein the at least one skin characteristic measurement device is a camera and the one or more passive skin characteristic measurement assisters comprise a lens, disposed in front of the camera when the enclosure is connected to the electronic device.

3. The skin analysis device of claim 1 wherein the at least one skin characteristic measurement device is a camera and the one or more passive skin characteristic measurement assisters comprise a color calibrator assembly, disposed in front of the camera when the enclosure is connected to the electronic device.

4. The skin analysis device of claim 3 wherein the color calibrator assembly comprises: a sleeve, through which the camera takes a picture, a color calibrator disposed on an inside surface of the sleeve, and a skin contact ring.

5. The skin analysis device of claim 1 wherein the at least one skin characteristic measurement device is a camera and the one or more passive skin characteristic measurement assisters comprise a light source assembly, wherein the light source assembly comprises: a light source board with one or more individually controllable light sources thereon that illuminate the user when the camera captures an image of the user; a diffuser that diffuses one or more light sources that pass through the diffuser, the light source board comprising one or more light source apertures located therein that allow light sources to pass therethrough undiffused; a set of first light sources providing a first light source, disposed on the light source board such that the first light source does not pass through the light source apertures and is diffused by the diffuser.

6. The skin analysis device of claim 5 wherein the light source assembly further comprises a set of second light sources providing a second light source, disposed on the light source board such that the second light source passes through the light source apertures undiffused.

7. The skin analysis device of claim 6 wherein the first light source is a light emitting diode (LED) light source and the second light source is an ultraviolet (UV) light source.

8. The skin analysis device of claim 6 wherein the set of first light sources are light emitting diode lights providing light emitting diode light and the set of second light sources are ultraviolet lights providing ultraviolet light.

9. The skin analysis device of claim 8 wherein the diffuser is configured to be between the light source board and the user, and configured to diffuse the first light source and not diffuse the second light source.

10. The skin analysis device of claim 1 further comprising: one or more active skin characteristic measurement assisters, connected to the enclosure and configured to assist the one or more skin characteristic measurement devices take a skin characteristic sample of a skin characteristic of the user; and a skin analysis device processor, in communication with the electronic device and the one or more active skin characteristic measurement assisters, the skin analysis device processor configured to: receive a sample taking signal from the electronic device; and control the one or more active skin characteristic measurement assisters to assist the one or more skin characteristic measurement devices in taking a skin characteristic sample.

11. The skin analysis device of claim 10 wherein the one or more active skin characteristic measurement assisters comprise a light source assembly.

12. The skin analysis device of claim 10 wherein the skin analysis device processor further comprises a Bluetooth transceiver and the sample taking signal is received from a Bluetooth transceiver of the electronic device.

13. The skin analysis device of claim 1 wherein the skin analysis device processor is further configured to: receive a sample taking signal from the electronic device; and control the second skin characteristic measurement device to take the second skin characteristic sample.

14. The skin analysis device of claim 13 wherein the skin analysis device processor further comprises a Bluetooth transceiver and the sample taking signal is received from a Bluetooth transceiver of the electronic device.

15. The skin analysis device of claim 1 wherein the enclosure further comprises a cylindrical sleeve assembly aperture configured to be disposed in front of a camera of the electronic device when the skin analysis device is attached to the electronic device.

16. The skin analysis device of claim 15 wherein the cylindrical sleeve assembly aperture is further configured to receive a skin characteristic measurement assister.

17. The skin analysis device of claim 1 further comprising an app, installed and operating on the electronic device, configured to: communicate with the skin analysis device and the electronic device to facilitate obtaining the skin characteristic sample from the at least one skin characteristic measurement device.

18. The skin analysis device of claim 1 wherein the calibrating the moisture sensor using a sensor autofocus distance calibration further comprises:
determining a second autofocus distance using an autofocus of the skin analysis device as the device takes a second moisture sensor reading when the user firmly touches the skin analysis device to their skin;
determining a third autofocus distance using the autofocus of the skin analysis device as the device takes a third moisture reading, when a user gently touches the skin analysis device to their skin; and
calculating an equation that best correlates the second autofocus distance, second moisture sensor reading, third autofocus distance and third moisture sensor reading.

* * * * *